(12) United States Patent
Xing et al.

(10) Patent No.: US 8,394,794 B2
(45) Date of Patent: Mar. 12, 2013

(54) THERAPEUTIC COMPOUNDS

(75) Inventors: Chengguo Xing, St. Paul, MN (US); Jignesh Doshi, St. Paul, MN (US)

(73) Assignee: Regents of The University of Minnesota, St. Paul, MN (US)

( * ) Notice: Subject to any disclaimer, the term of this patent is extended or adjusted under 35 U.S.C. 154(b) by 490 days.

(21) Appl. No.: 12/532,804

(22) PCT Filed: Mar. 21, 2008

(86) PCT No.: PCT/US2008/057892
§ 371 (c)(1),
(2), (4) Date: Apr. 5, 2010

(87) PCT Pub. No.: WO2008/118802
PCT Pub. Date: Oct. 2, 2008

(65) Prior Publication Data
US 2010/0197686 A1 Aug. 5, 2010

Related U.S. Application Data

(60) Provisional application No. 60/919,746, filed on Mar. 23, 2007.

(51) Int. Cl.
| | | |
|---|---|---|
| *A61K 31/5377* | (2006.01) | |
| *A61K 31/353* | (2006.01) | |
| *A61K 31/453* | (2006.01) | |
| *A61K 31/497* | (2006.01) | |
| *A61K 31/404* | (2006.01) | |
| *A61K 31/423* | (2006.01) | |
| *A61K 31/416* | (2006.01) | |
| *A61K 31/4709* | (2006.01) | |
| *C07D 311/74* | (2006.01) | |
| *C07D 405/06* | (2006.01) | |
| *C07D 413/06* | (2006.01) | |
| *C07D 405/10* | (2006.01) | |
| *C07D 263/52* | (2006.01) | |
| *C07D 231/56* | (2006.01) | |
| *C07D 215/02* | (2006.01) | |

(52) U.S. Cl. ............... 514/233.5; 514/254.11; 514/314; 514/320; 514/375; 514/406; 514/414; 514/456; 544/151; 544/376; 546/173; 546/196; 548/217; 548/361.1; 548/454; 549/404

(58) Field of Classification Search ............... 514/233.5, 514/254.11, 314, 320, 375, 406, 414, 456; 544/151, 376; 546/173, 196; 548/217, 361.1, 548/454; 549/404
See application file for complete search history.

(56) References Cited

U.S. PATENT DOCUMENTS
6,492,389 B1* 12/2002 Huang et al. ............... 514/311
2006/0035925 A1 2/2006 Cai et al.

OTHER PUBLICATIONS

Junek et al. "CAS Accession No. 1967:85672" 1967.*

Curini et al. "Preparation of 2-Amino-4H-chromene Derivatives from Coumarins in Basic Media" European Journal of Organic Chemistry, 2006, vol. 2006, No. 3, pp. 746-751.*
Tian et al. "sHA 14-1, a stable and ROS-free antagonist against anti-apoptotic Bcl-2 proteins, bypasses drug resistances and synergizes cancer therapies in human leukemia cell" Cancer Letters, 2008, vol. 259, pp. 198-208.*
An et al., "Critical Upstream Signals of Cytochrome *c* Release Induced by a Novel Bcl-2 Inhibitor", *J. Biol. Chem.*, 279(18), 19133-19140 (2004).
Di Lorenzo et al., "Docetaxel, Vinorelbine, and Zoledronic Acid as First-Line Treatment in Patients with Hormone Refractory Prostate Cancer: A Phase II Study", *European Urology* 52, 1020-1027 (2007).
Doshi et al., "Structure-Actvity Relationship Studies of Ethyl-2-Amino-6-bromo-4-(1-cyano-2-ethoxy-2-oxoethyl)-4*H*-chromene-3-carboxylate (HA 14-1), an Antagonist for Anti-apoptotic Bcl-2 Proteins to Overcome Drug Resistance in Cancer", *J. Med. Chem.*, 49(26), 7731-7739 (2006).
Gapud et al., "Laulimalide and Paclitaxel: A Comparison of Their Effects on Tubulin Assembly and Their Synergistic Action when Present Simultaneously", *Mol. Pharmacol*, 66 113-121 (2004).
Goodin et al., "A phase II trial of docetaxel and vinorelbine in patients with hormone-refractory prostate cancer", *Cancer Chemother Pharmacol*, 56, 199-204 (2005).
Huang et al., "Potentiation of Taxol Efficacy by Discodermolide in Ovarian Carcinoma Xenograft-Bearing Mice", *Clin. Cancer Res.*, 12 (1), 298-304 (2006).
Lavelle et al., "Preclinical Evaluation of Docetaxel (Taxotere)", *Semin. Oncol.*, 22. (2 Suppl 4), 3-16, (1995).

(Continued)

*Primary Examiner* — Joseph Kosack
(74) *Attorney, Agent, or Firm* — Viksnins Harris & Padys PLLP

(57) ABSTRACT

The invention provides compounds of Formula (I) and (IV): as described herein, as well as salts thereof. The compounds have anti-cancer properties and/or chemosensitization properties.

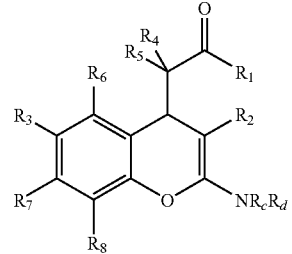

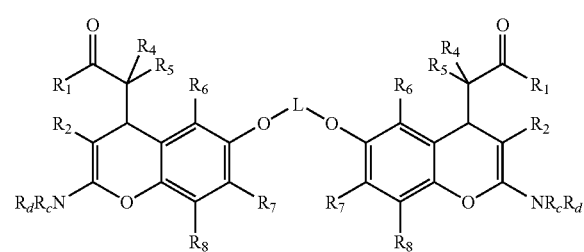

21 Claims, 7 Drawing Sheets

OTHER PUBLICATIONS

Martello et al., "Taxol and Discodermolide Represent a Synergistic Drug Combination in Human Carcinoma Cell Lines", *Clin. Cancer Res.*, 6, 1978-1987 (2000).

Patent Cooperation Treaty, International Search Report and Written Opinion of the International Searching Authority, PCT/US2008/57892, 10 pages, Jun. 25, 2008.

Sewak, "A phase I study of paclitaxel, estramustine phosphate and vinorelbine (Pacl-E-Vin) in advanced malignancies: triple tubulin targeting", *Anti-Cancer Drugs*, 14, 67-72 (2003).

Tolcher et al., "A Phase I Pharmacokinetic and Biological Correlative Study of Oblimersen Sodium (Genasense, G3139), an Antisense Oligonucleotide to the Bcl-2 mRNA, and of Docetaxel in Patients with Hormone-Refractory Prostate Cancer", *Clin. Cancer Res.*, 10, 5048-5057 (2004).

Tolcher et al., "A Phase II, Pharmacokinetic, and Biological Correlative Study of Oblimersen Sodium and Docetaxel in Patients with Hormone-Refractory Prostate Cancer", *Clin. Cancer Res.*, 11 (10), 3854-3861 (2005).

Xu et al., "(--)-Gossypol enhances response to radiation therapy and results in tumor regression of human prostate cancer", *Mol. Cancer Ther.*, 4 (2), 197-205 (2005).

\* cited by examiner

THERAPEUTIC COMPOUNDS

RELATED APPLICATIONS

This application is a National Stage application under 35 U.S.C. §371 of International Application No. PCT/US2008/057892 having an International Filing Date of Mar. 21, 2008 and claims priority to U.S. Provisional Application No. 60/919,746, which was filed on Mar. 23, 2007.

BACKGROUND OF THE INVENTION

Apoptosis is a naturally occurring process of cellular suicide that helps maintain homeostasis by eliminating damaged cells. However, in certain diseased states such as cancer, apoptosis is impaired leading to increased survival of the cancerous cells. A major obstacle in the treatment of cancer today is the development of resistance to various chemotherapeutic agents. Elevated levels of the anti-apoptotic Bcl-2 proteins are one of the major contributors to this observed drug resistance. Antagonizing the effect of these proteins would thereby diminish the barrier to apoptosis and aid in overcoming the drug resistance induced by these proteins.

Various small organic compounds have been demonstrated to antagonize these anti-apoptotic proteins and induce the cells to apoptosis. Of these compounds, HA 14-1 is a promising agent as it has shown the capability to selectively eliminate tumors with elevated levels of the anti-apoptotic proteins.

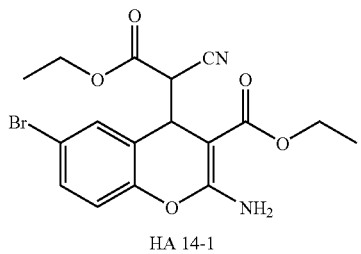 [SMILES: CCOC(=O)C1=C(N)Oc2ccc(Br)cc2C1C(C#N)C(=O)OCC]

HA 14-1

Moreover, HA 14-1 can also sensitize cancer cells to a wide range of cancer therapies, suggesting a therapeutic potential for development as a chemosensitizer. An advantage of such an approach is the reduction in the dose and associated side-effects of the cancer therapies. Unfortunately, the clinical use of HA 14-1 may be limited due to it's lack of stability under physiological conditions.

Currently, there is a need for therapeutic agent that is useful for treating cancer.

SUMMARY OF THE INVENTION

The present invention provides compounds that possess anti-cancer activity and/or activity as chemosensitizers. Accordingly in one embodiment of the invention there is provided a compound of the invention which is a compound of formula (I):

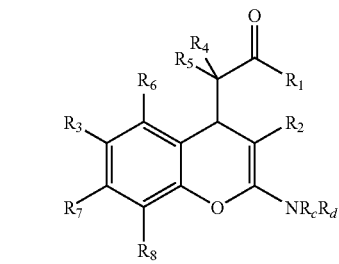

wherein:
$R_1$ is $(C_1$-$C_6)$alkoxy or $NR_aR_b$;
$R_2$ is cyano, $(C_1$-$C_6)$alkoxycarbonyl or —$C(O)NR_eR_f$;
Each of $R_3$, $R_6$, $R_7$ and $R_8$ is independently hydrogen, halo, cyano, $(C_1$-$C_6)$alkyl, cycloalkyl, aryl, heteroaryl, aryl$(C_1$-$C_6)$alkyl or $(C_1$-$C_6)$alkoxycarbonyl;
$R_c$ and $R_d$ are independently hydrogen, $(C_1$-$C_6)$alkyl, $(C_1$-$C_6)$alkanoyl or arylcarbonyl; or $R_c$ and $R_d$ taken together with the nitrogen to which they are attached form a pyrrolidino, piperidino, piperazino, or morpholino ring;
$R_e$ and $R_f$ are independently hydrogen or $(C_1$-$C_6)$alkyl; or $R_c$ and $R_d$ taken together with the nitrogen to which they are attached form a pyrrolidino, piperidino, piperazino, or morpholino ring;
$R_4$ and $R_5$ are each hydrogen; or $R_4$ is $(C_1$-$C_6)$alkyl and $R_5$ is cyano;
$R_a$ and $R_b$ are independently hydrogen or $(C_1$-$C_6)$alkyl; or $R_a$ and $R_b$ taken together with the nitrogen to which they are attached form a pyrrolidino, piperidino, piperazino, or morpholino ring;
wherein any aryl or heteroaryl of $R_3$, $R_6$, $R_7$ or $R_8$ is optionally substituted with one or more (e.g. 1, 2, 3, or 4) groups independently selected from halo, hydroxy, cyano, $CF_3$, $OCF_3$, $OCHF_2$, $(C_1$-$C_6)$alkyl, $(C_1$-$C_6)$alkoxy, $(C_1$-$C_6)$alkanoyl, aryloxy, $NR_gR_h$, benzyloxy, $(C_1$-$C_6)$alkoxycarbonyl, and $(C_1$-$C_6)$alkanoyloxy; and
each $R_g$ and $R_h$ is independently hydrogen or $(C_1$-$C_6)$alkyl; or $R_g$ and $R_h$ taken together with the nitrogen to which they are attached form a pyrrolidino, piperidino, piperazino, or morpholino ring;
or a salt thereof.

In another embodiment of the invention there is provided a compound of the invention which is a compound of formula (II):

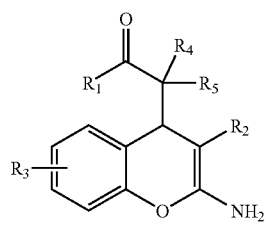

wherein:
$R_1$ is $(C_1$-$C_6)$alkoxy or $NR_aR_b$;
$R_2$ is cyano, or $(C_1$-$C_6)$alkoxycarbonyl;
$R_3$ is hydrogen, halo, $(C_1$-$C_6)$alkyl, aryl, aryl$(C_1$-$C_6)$alkyl, cyano, or $(C_1$-$C_6)$alkoxycarbonyl;
$R_4$ and $R_5$ are each hydrogen; or $R_4$ is $(C_1$-$C_6)$alkyl and $R_5$ is cyano; and each $R_a$ and $R_b$ is independently hydrogen or $(C_1-C_6)$alkyl; or $R_a$ and $R_b$ taken together with the nitrogen to which they are attached form a pyrrolidino, piperidino, piperazino, or morpholino ring;

wherein any aryl of $R_3$ is optionally substituted with one or more (e.g. 1, 2, 3, or 4) groups independently selected from halo, hydroxy, $(C_1-C_6)$alkyl, $(C_1-C_6)$alkoxy, $(C_1-C_6)$alkoxycarbonyl, and $(C_1-C_6)$alkanoyloxy;

or a salt thereof.

In another embodiment of the invention there is provided a compound of the invention which is a compound of formula (III):

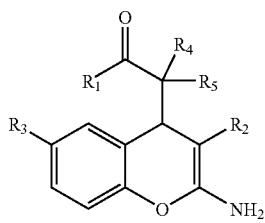

wherein:
$R_1$ is $(C_1-C_6)$alkoxy or $NR_aR_b$;
$R_2$ is cyano, or $(C_1-C_6)$alkoxycarbonyl;
$R_3$ is hydrogen, halo, $(C_1-C_6)$alkyl, aryl, aryl$(C_1-C_6)$alkyl, cyano, or $(C_1-C_6)$alkoxycarbonyl;
$R_4$ and $R_5$ are each hydrogen; or $R_4$ is $(C_1-C_6)$alkyl and $R_5$ is cyano; and each $R_a$ and $R_b$ is independently hydrogen or $(C_1-C_6)$alkyl; or $R_a$ and $R_b$ taken together with the nitrogen to which they are attached form a pyrrolidino, piperidino, piperazino, or morpholino ring;

wherein any aryl of $R_3$ is optionally substituted with one or more (e.g. 1, 2, 3, or 4) groups independently selected from halo, hydroxy, $(C_1-C_6)$alkyl, $(C_1-C_6)$alkoxy, $(C_1-C_6)$alkoxycarbonyl, and $(C_1-C_6)$alkanoyloxy;

or a salt thereof.

In another embodiment of the invention there is provided a compound of the invention which is a compound of formula (IV):

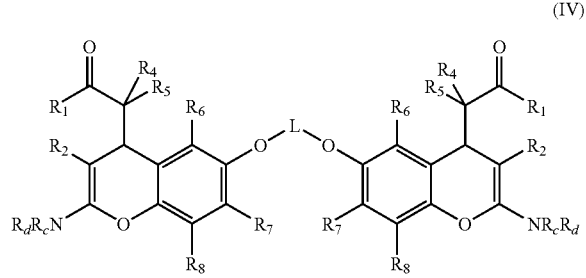

wherein:
L is $-(CH_2)_n-$;
n is 1, 2, 3, 4, 5, or 6; and
$R_1$ is $(C_1-C_6)$alkoxy or $NR_aR_b$;
$R_2$ is cyano, $(C_1-C_6)$alkoxycarbonyl or $-C(O)NR_eR_f$;
each of $R_6$, $R_7$ and $R_8$ is independently hydrogen, halo, cyano, $(C_1-C_6)$alkyl, cycloalkyl, aryl, heteroaryl, aryl$(C_1-C_6)$alkyl or $(C_1-C_6)$alkoxycarbonyl;

$R_c$ and $R_d$ are independently hydrogen, $(C_1-C_6)$alkyl, $(C_1-C_6)$alkanoyl or arylcarbonyl; or $R_c$ and $R_d$ taken together with the nitrogen to which they are attached form a pyrrolidino, piperidino, piperazino, or morpholino ring;

$R_e$ and $R_f$ are independently hydrogen or $(C_1-C_6)$alkyl; or $R_c$ and $R_d$ taken together with the nitrogen to which they are attached form a pyrrolidino, piperidino, piperazino, or morpholino ring;

$R_4$ and $R_5$ are each hydrogen; or $R_4$ is $(C_1-C_6)$alkyl and $R_5$ is cyano;

$R_a$ and $R_b$ are independently hydrogen or $(C_1-C_6)$alkyl; or $R_a$ and $R_b$ taken together with the nitrogen to which they are attached form a pyrrolidino, piperidino, piperazino, or morpholino ring;

wherein any aryl or heteroaryl of $R_3$, $R_6$, $R_7$ or $R_8$ is optionally substituted with one or more (e.g. 1, 2, 3, or 4) groups independently selected from halo, hydroxy, cyano, $CF_3$, $OCF_3$, $OCHF_2$, $(C_1-C_6)$alkyl, $(C_1-C_6)$alkoxy, $(C_1-C_6)$alkanoyl, aryloxy, $NR_gR_h$, benzyloxy, $(C_1-C_6)$alkoxycarbonyl, and $(C_1-C_6)$alkanoyloxy; and each $R_g$ and $R_h$ is independently hydrogen or $(C_1-C_6)$alkyl; or $R_g$ and $R_h$ taken together with the nitrogen to which they are attached form a pyrrolidino, piperidino, piperazino, or morpholino ring;

or a salt thereof.

In another embodiment of the invention there is provided a compound of the invention which is a compound of formula (V):

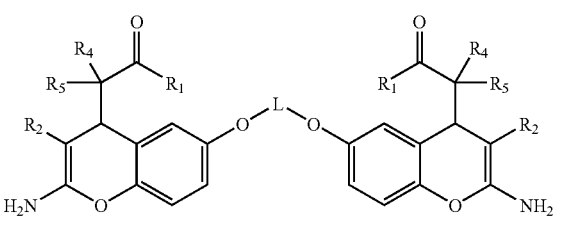

wherein:
$R_1$ is $(C_1-C_6)$alkoxy or $NR_aR_b$;
$R_2$ is cyano or $(C_1-C_6)$alkoxycarbonyl;
$R_4$ and $R_5$ are each hydrogen; or $R_4$ is $(C_1-C_6)$alkyl and $R_5$ is cyano;
L is $-(CH_2)_n-$;
n is 1, 2, 3, 4, 5, or 6; and
each $R_a$ and $R_b$ is independently hydrogen or $(C_1-C_6)$alkyl; or $R_a$ and $R_b$ taken together with the nitrogen to which they are attached form a pyrrolidino, piperidino, piperazino, or morpholino ring;

or a salt thereof.

In another embodiment the invention provides a compound of the following formula:

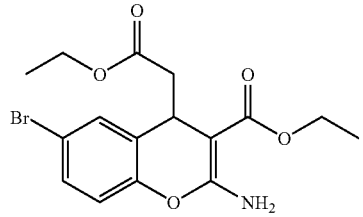

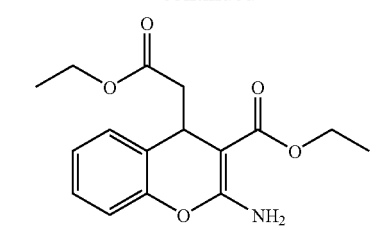
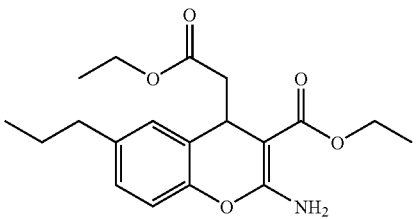
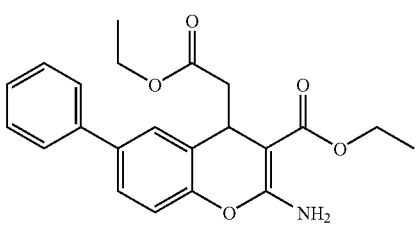
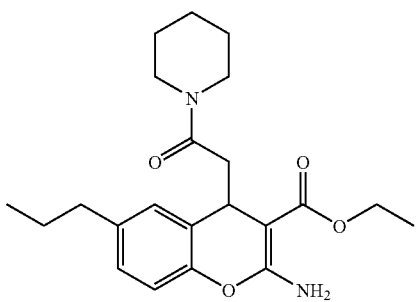 [SMILES: CCCc1ccc2c(c1)C(CC(=O)N1CCCCC1)C(C(=O)OCC)=C(N)O2]
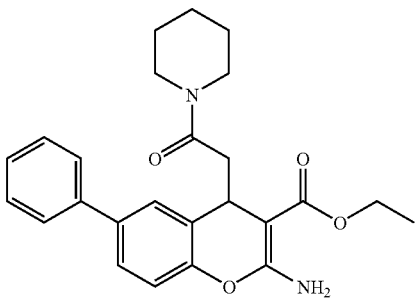
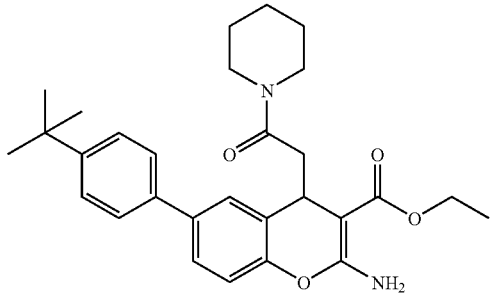 [SMILES: CCOC(=O)C1=C(N)Oc2ccc(-c3ccc(C(C)(C)C)cc3)cc2C1CC(=O)N1CCCCC1]
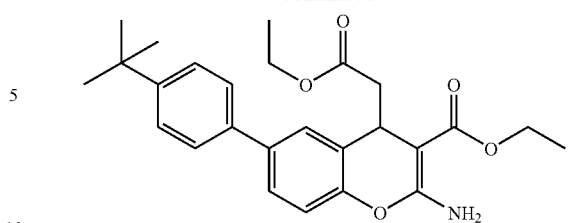
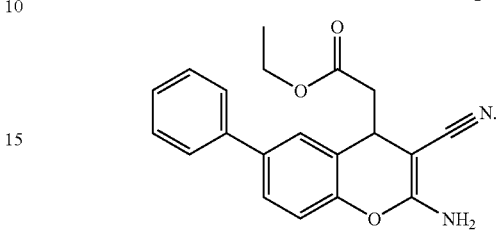
or a salt thereof.
In another embodiment the invention provides a compound of the following formula:
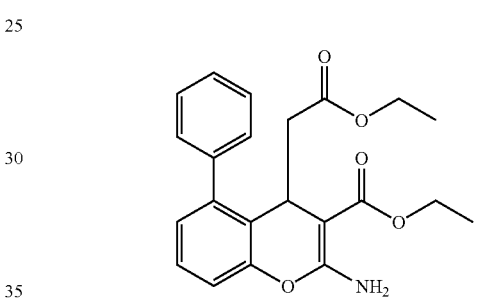
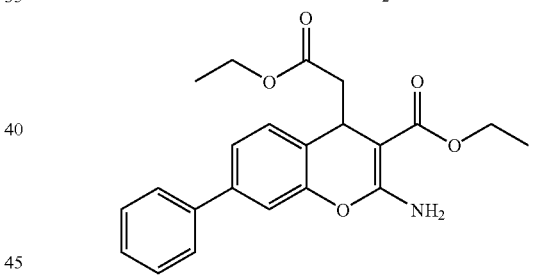
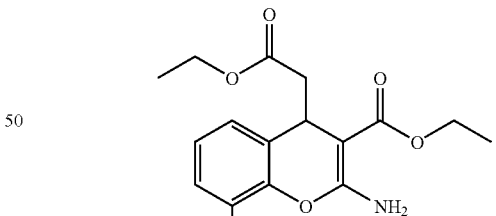
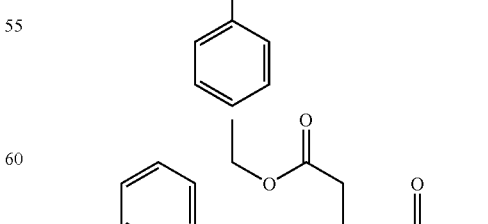
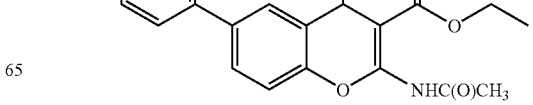

-continued
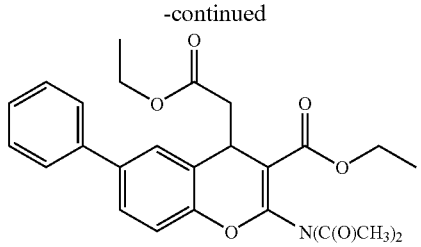
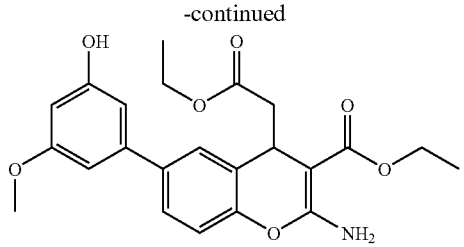
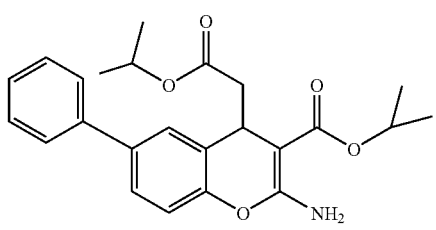
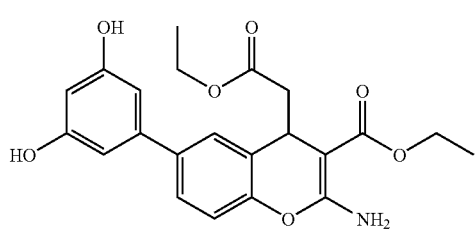
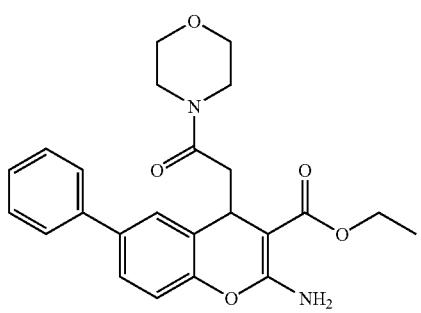
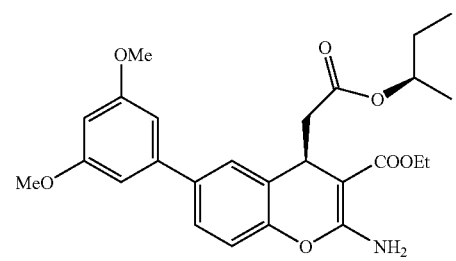
or a salt thereof.
In another embodiment the invention provides a compound of the following formula:
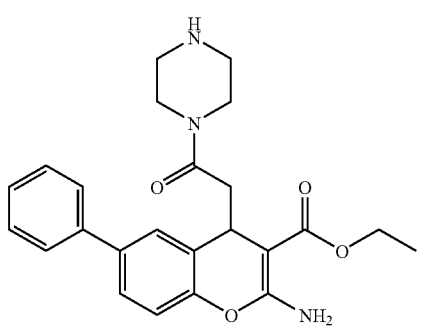
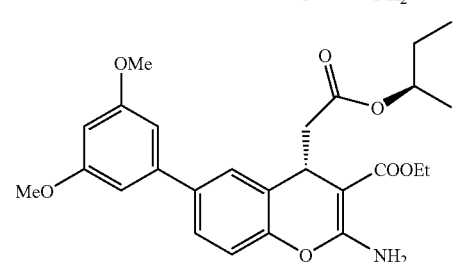
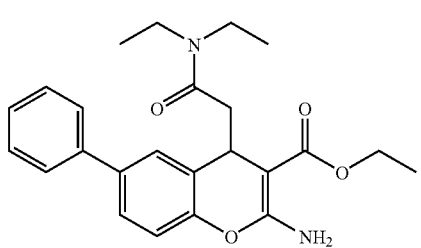
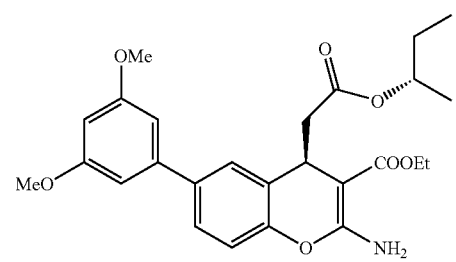
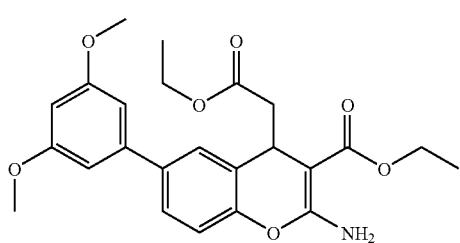
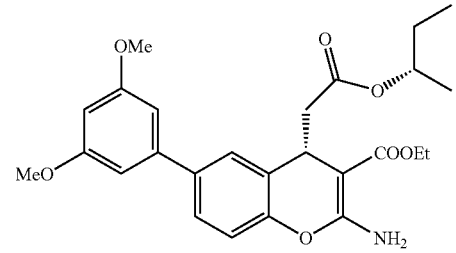

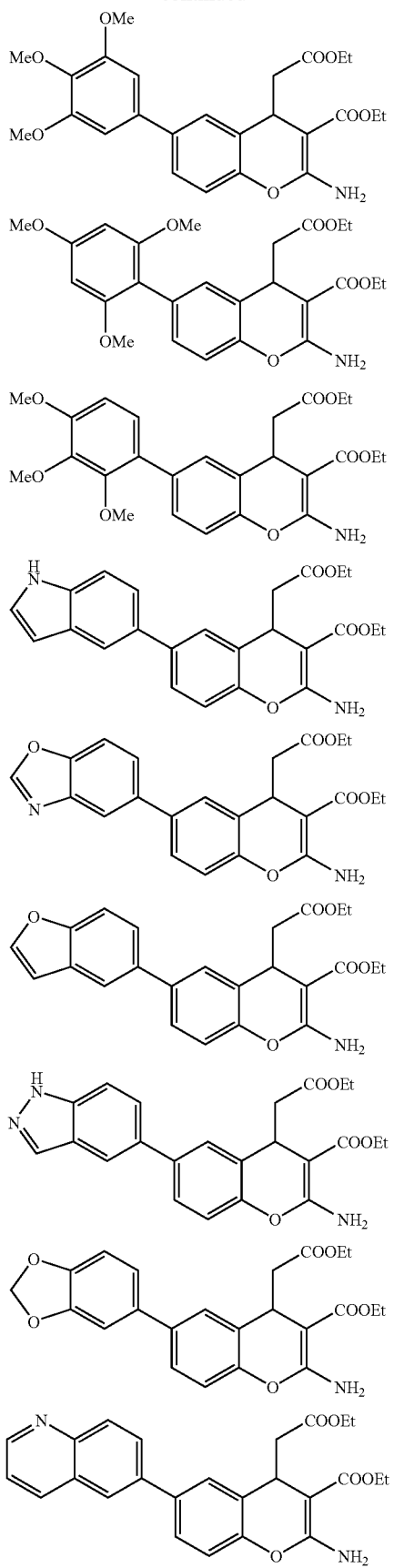
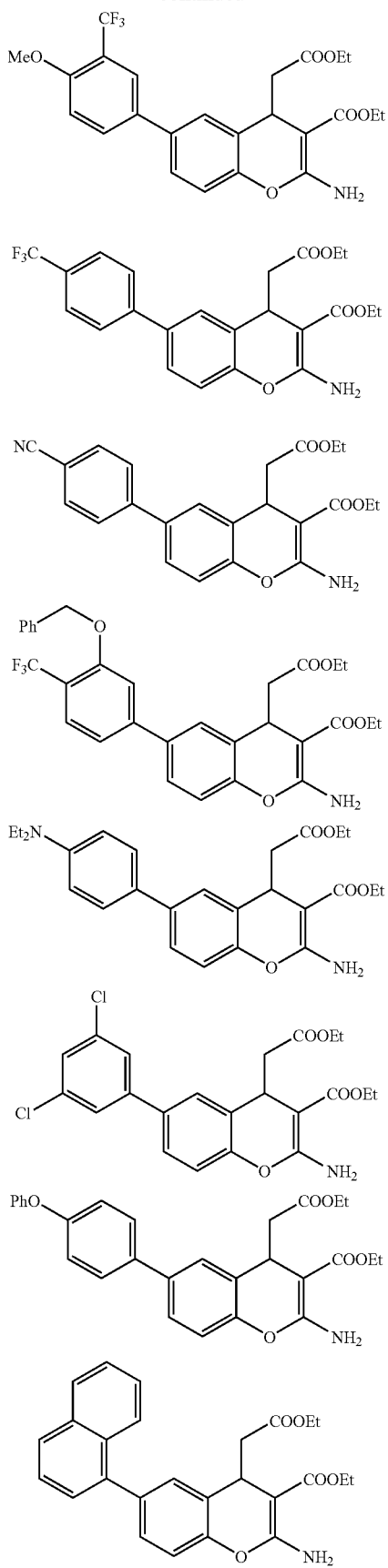

-continued

[Chemical structures shown:
- 4-acetylphenyl-substituted chromene with COOEt groups and NH2
- 4-isopropyl-2-methoxyphenyl-substituted chromene with COOEt groups and NH2
- 3,5-dimethoxyphenyl-substituted chromene with COOEt groups and NHCOPh]

or a salt thereof.

The invention also provides a pharmaceutical composition comprising a compound of formula (I), (II), (III), (IV) or (V) or a pharmaceutically acceptable salt thereof, in combination with a pharmaceutically acceptable diluent or carrier. In another embodiment, the composition can optionally comprise one or more additional therapeutic agents (e.g. anti-cancer agents).

The invention also provides a therapeutic method for treating a pathological condition or symptom in a mammal wherein the activity of Bcl-2 protein is implicated and antagonism of its action is desired comprising administering a compound of formula (I), (II), (III), (IV) or (V), or a pharmaceutically acceptable salt thereof to the mammal.

The invention also provides a method for treating cancer in a mammal comprising administering a compound of formula (I), (II), (III), (IV) or (V), or a pharmaceutically acceptable salt thereof to the mammal.

The invention also provides a method of sensitizing cancer cells to therapy comprising contacting (in vivo or in vitro) the cells with a compound of formula (I), (II), (III), (IV) or (V), or a pharmaceutically acceptable salt thereof.

The invention also provides a compound of formula (I), (II), (III), (IV) or (V), or a pharmaceutically acceptable salt thereof for use in medical therapy.

The invention also provides the use of a compound of formula (I), (II), (III), (IV) or (V), or a pharmaceutically acceptable salt thereof, for the manufacture of a medicament useful for treating a pathological condition or symptom in a mammal wherein the activity of Bcl-2 protein is implicated and antagonism of its action is desired.

The invention also provides the use of a compound of formula (I), (II), (III), (IV) or (V), or a pharmaceutically acceptable salt thereof for the manufacture of a medicament useful for treating cancer in a mammal.

The invention also provides the use of a compound of formula (I), (II), (III), (IV) or (V), or a pharmaceutically acceptable salt thereof for the manufacture of a medicament useful for sensitizing cancer cells to therapy.

The invention also provides a compound of formula (I), (II), (III), (IV) or (V), or a pharmaceutically acceptable salt thereof, for use in the prophylactic or therapeutic treatment of a pathological condition or symptom wherein the activity of Bcl-2 protein is implicated and antagonism of its action is desired.

The invention also provides a compound of formula (I), (II), (III), (IV) or (V), or a pharmaceutically acceptable salt thereof, for use in the prophylactic or therapeutic treatment of cancer.

The invention also provides a compound of formula (I), (II), (III), (IV) or (V), or a pharmaceutically acceptable salt thereof, for sensitizing cancer cells to therapy.

The invention also provides processes and intermediated disclosed herein that are useful for preparing compounds of formula (I), (II), (III), (IV) or (V), or salts thereof.

DETAILED DESCRIPTION

Figure 1:
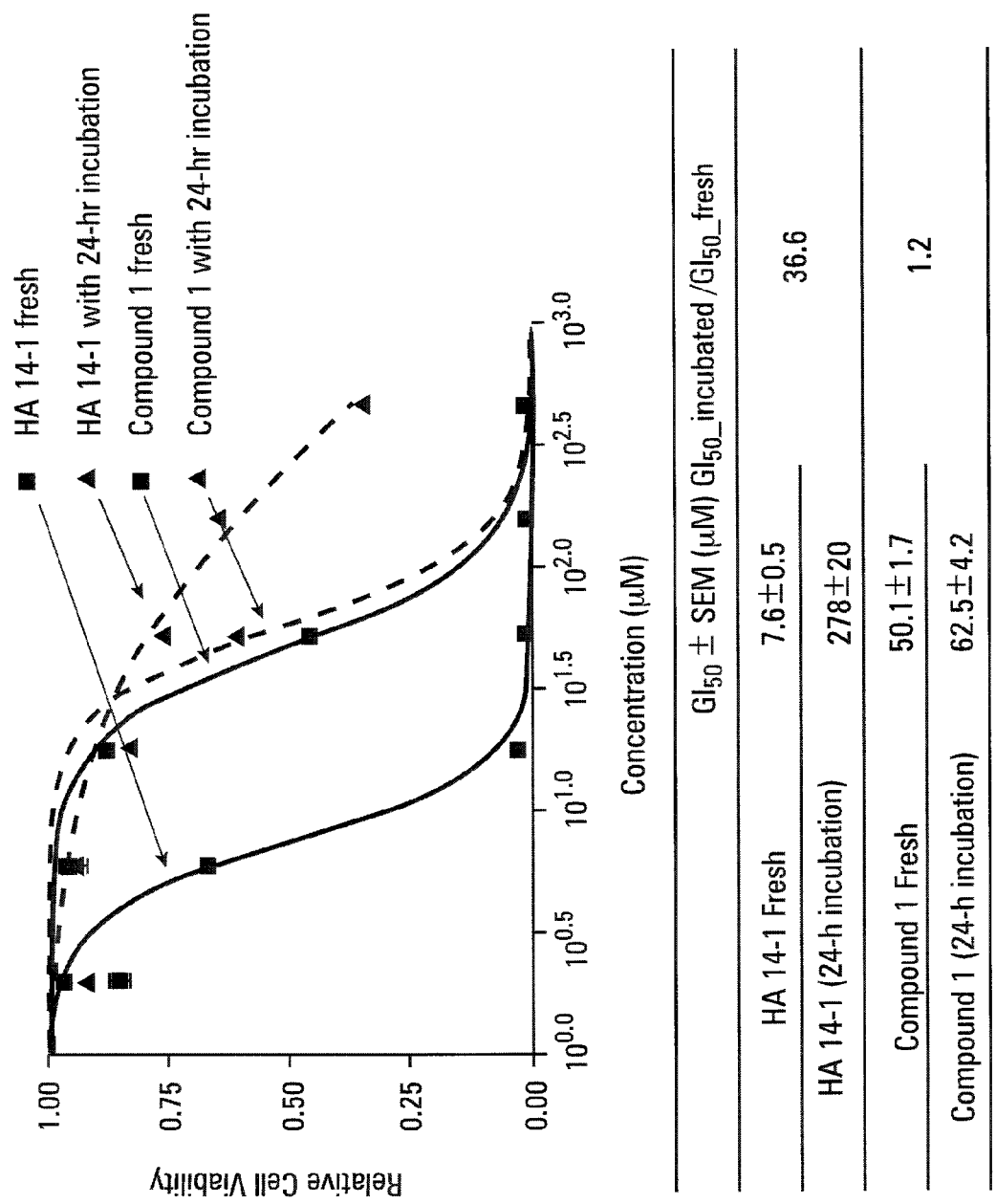
FIG. 1 illustrates the relative loss of cytotoxicity of HA 14-1 and compound 1 upon incubation in cell culture media.

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

The term "heteroaryl" as used herein refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms. The nitrogen heteroatom my be optionally substituted with ($C_1$-$C_6$)alkyl, phenyl and benzyl. Such heteroaryl groups can have a single ring (e.g., pyridyl, pyrazole or furyl) or multiple condensed rings (e.g., indolyl, indazolyl, quinolinyl, benzoxazolyl or benzofuranyl) wherein at least one of the condensed rings is aromatic. Exemplary heteroaryl groups include, but are not limited to pyridyl, pyrrolyl, thienyl, indolyl, thiophenyl, 3,4-methylenedioxyphenyl, and furyl.

The term "cycloalkyl" as used herein refers to a mono or poly cyclic hydrocarbon ring system, such as one containing 3 to 10 carbon atoms. Exemplary groups include but are not limited to cyclopropyl, cyclobutyl, cyclopentyl, cyclohexyl, cycloheptyl, and adamantyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, iso-propoxy, butoxy, iso-butoxy, sec-butoxy, pentoxy, 3-pentoxy, or hexyloxy; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; and aryl can be phenyl, indenyl, or naphthyl.

A specific value for $R_1$ is $(C_1-C_6)$alkoxy.
A specific value for $R_1$ is $NR_aR_b$.
A specific value for $R_1$ is ethoxy or isopropoxy.
A specific value for $R_1$ is ethoxy.
A specific value for $R_1$ is piperidino.
A specific value for $R_1$ is morpholino.
A specific value for $R_1$ is piperazino.
A specific value for $R_1$ is diethylamino.
A specific value for $R_2$ is cyano.
A specific value for $R_2$ is $(C_1-C_6)$alkoxycarbonyl.
A specific value for $R_2$ is ethoxycarbonyl, isopropoxycarbonyl, or cyano.
A specific value for $R_2$ is ethoxycarbonyl.
A specific value for $R_3$ is hydrogen.
A specific value for $R_3$ is halo.
A specific value for $R_3$ is bromo.
A specific value for $R_3$ is $(C_1-C_6)$alkyl.
A specific value for $R_3$ is aryl, which is optionally substituted with one or more (e.g. 1, 2, 3, or 4) groups independently selected from halo, hydroxy, cyano, $CF_3$, $OCF_3$, $OCHF_2$, $(C_1-C_6)$alkyl, $(C_1-C_6)$alkoxy, $(C_1-C_6)$alkanoyl, aryloxy, $NR_gR_h$, benzyloxy, $(C_1-C_6)$alkoxycarbonyl, and $(C_1-C_6)$alkanoyloxy.
A specific value for $R_3$ is aryl, which is optionally substituted with one or more (e.g. 1, 2, 3, or 4) groups independently selected from halo, hydroxy, $(C_1-C_6)$alkyl, $(C_1-C_6)$alkoxy, $(C_1-C_6)$alkoxycarbonyl, and $(C_1-C_6)$alkanoyloxy.
A specific value for $R_3$ is phenyl, which is optionally substituted with one or more (e.g. 1, 2, 3, or 4) $(C_1-C_6)$alkyl groups.
A specific value for $R_3$ is hydrogen, bromo, propyl, phenyl, 4-tert-butylphenyl, 3-methoxy,5-hydroxyphenyl, 3,5-dihydroxyphenyl, or 3,5-dimethoxyphenyl.
A specific value for $R_3$ is hydrogen, bromo, propyl, phenyl, or 4-tert-butylphenyl.
A specific value for $R_4$ and $R_5$ are each hydrogen.
A specific value for $R_4$ is $(C_1-C_6)$alkyl and for $R_5$ is cyano.

Processes for preparing compounds of formula (I), (II), (III), (IV) and (V) are provided as further embodiments of the invention.

Generally, compounds of formula (I), (II) and (III) wherein $R_1$ is $(C_1-C_6)$alkoxy can be prepared as illustrated in the following scheme.

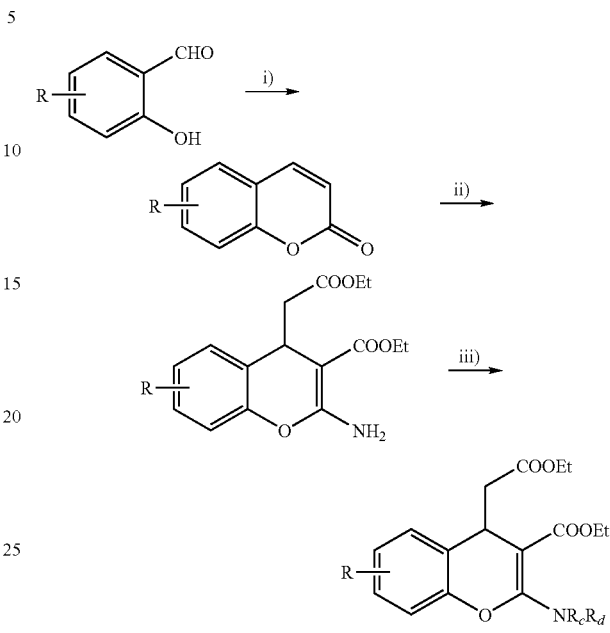

i) N,N-Dimethylacetamide, POCl$_3$, dry CH$_2$Cl$_2$, reflux; ii) NaOEt, Ethyl cyanoacetate, EtOH, rt; iii) R$_c$X or R$_d$X, Base Generally, compounds of formula (I), (II) and (III) wherein $R_1$ is $NR_aR_b$ can be prepared as illustrated in the following scheme.

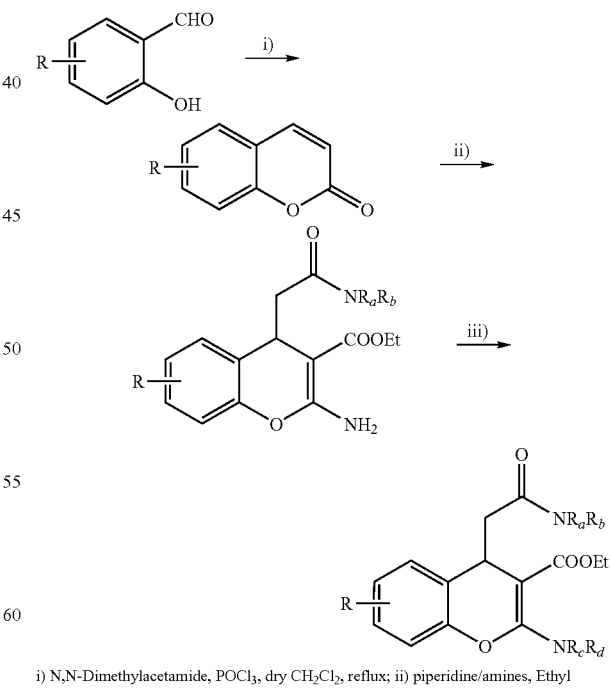

i) N,N-Dimethylacetamide, POCl$_3$, dry CH$_2$Cl$_2$, reflux; ii) piperidine/amines, Ethyl cyanoacetate, rt; iii) R$_c$X or R$_d$X, Base Generally, compounds of formula (IV) and (V) can be prepared as illustrated in the following scheme.

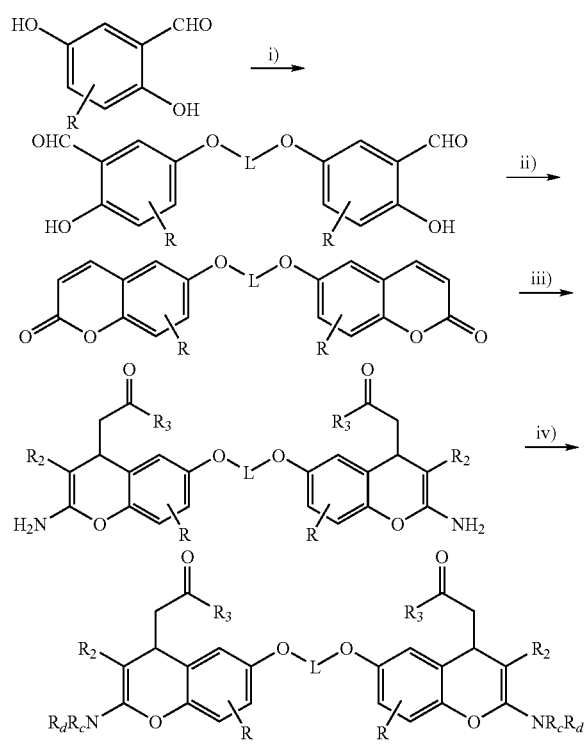

i) 1,2-dichloroethane, NaOH; ii) N,N-Dimethylacetamide, POCl₃, dry CH₂Cl₂, reflux; iii) piperidine/amines, Ethyl cyanoacetate, rt; iv) $R_cX$ or $R_dX$, Base.

In cases where compounds are sufficiently basic or acidic, a salt of a compound can be useful as an intermediate for isolating or purifying the corresponding compound. Additionally, administration of a compound of formula (I), (II), (III), (IV), or (V) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608, 392), Geria (U.S. Pat. No. 4,992,478), Smith et al. (U.S. Pat. No. 4,559,157) and Wortzman (U.S. Pat. No. 4,820,508).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Accordingly, in one embodiment the invention also provides a composition comprising a compound of formula (I), (II), (III), (IV, or (V) or a pharmaceutically acceptable salt thereof, at least one other therapeutic agent, and a pharmaceutically acceptable diluent or carrier. The invention also provides a kit comprising a compound of formula (I), (II), (III), (IV), or (V) or a pharmaceutically acceptable salt thereof, at least one other therapeutic agent, packaging material, and instructions for administering the compound or the pharmaceutically acceptable salt thereof and the other therapeutic agent or agents to an animal to treat cancer.

Compound 1 (Example 2) was first evaluated for its stability under physiological conditions. In brief, compound 1 was incubated in cell culture media at 37° C. for 24 hours and the in vitro cytotoxicity was determined. HA 14-1 was run in parallel for comparison. As shown in FIG. 1, 24-hour incubation resulted in ~35-fold increase of $GI_{50}$ of HA 14-1 because of its decomposition/deactivation. Compound 1, however, exhibited only 1.2-fold increase of $GI_{50}$, indicating that compound 1 is much more stable than HA 14-1 under physiological conditions. This is further supported by the HPLC analysis of the decomposition of compound 1 that no decomposition was detected with 48-hour incubation of compound 1 in cell culture media at 37° C.

With the stability improved, the mechanism of action of compound 1 was studied to determine whether compound 1 would retain the same mechanism of HA 14-1 as an antagonist against anti-apoptotic Bcl-2 proteins. Table 1 summarizes the binding interaction of compound 1 with three anti-apoptotic Bcl-2 proteins by following an established fluorescence polarization competition assay (see Doshi, J. M.; Tian, D.; Xing, C. *J. Med. Chem.* 2006, 49, 7731-7739).

TABLE 1

Binding interactions of compound 1 and HA 14-1 to three anti-apoptotic Bcl-2 proteins.

| $K_i$ (µM) | Bcl-2 | Bcl-$X_L$ | Bcl-w |
| --- | --- | --- | --- |
| HA 14-1 | 169 ± 18.9 | 58.9 ± 5.3 | 59.3 ± 5.3 |
| Compound 1 | 858 | 390 | 686 |

Compound 1 has a weaker binding interactions with the three anti-apoptotic Bcl-2 proteins compared to HA 14-1, suggesting that the cyano functional group is involved in the binding interaction of HA 14-1 with anti-apoptotic Bcl-2 proteins.

Figure 2:
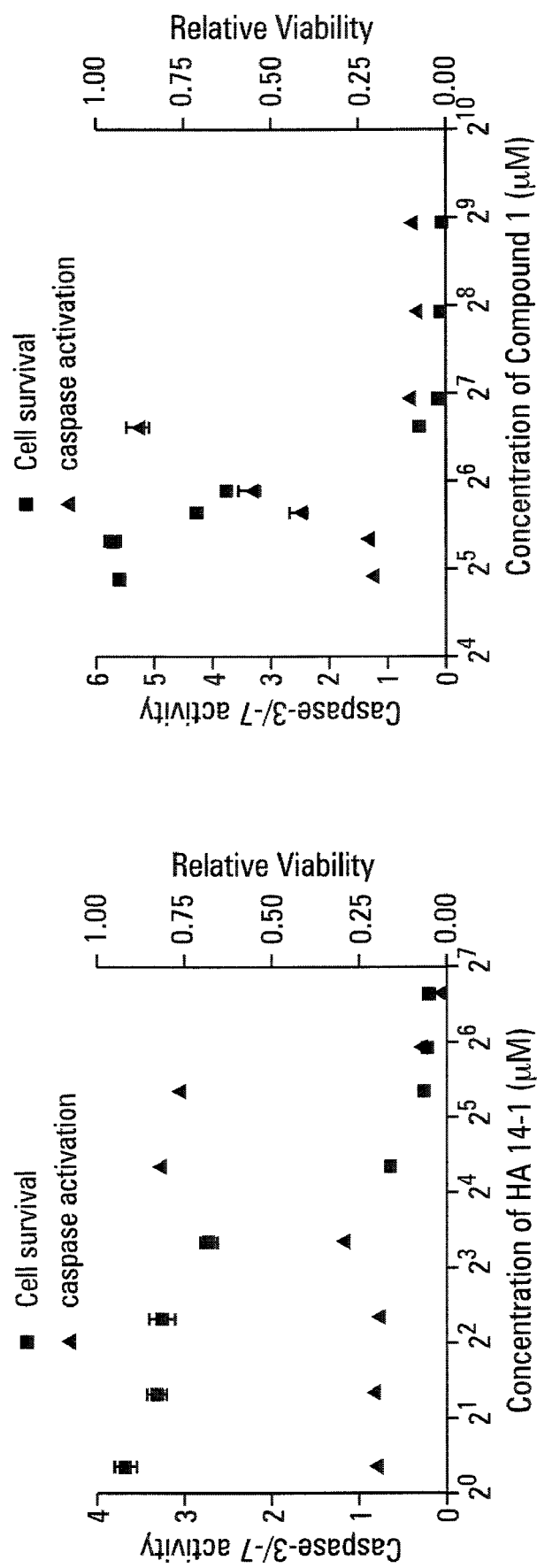
FIG. 2 depicts the inhibition of cell growth and activation of caspase-3/-7 induced by the treatment of HA 14-1 or compound 1 for 24 hours.

Compound 1 was further analyzed for its mechanism to inhibit cell growth as HA 14-1 does. This was characterized for concentration-dependent activation of caspase-3/-7. HA 14-1 was run in parallel for comparison. FIG. 2 demonstrated that compound 1 is less cytotoxic than HA 14-1, consistent with its weaker interaction with anti-apoptotic Bcl-2 proteins than HA 14-1.

Mechanistically, however, compound 1 induced cell death through two different pathways depending on its concentration, similar to HA 14-1. Between 50-100 μM, compound 1 induces apoptosis as characterized by caspase-3/-7 activation. On the other hand, at >100 μM, compound 1 induced non-apoptotic cell death (no activation of caspase-3/-7). The induction of cell death through apoptosis and non-apoptotic process was further supported by DNA fragmentation studies.

Figure 3:
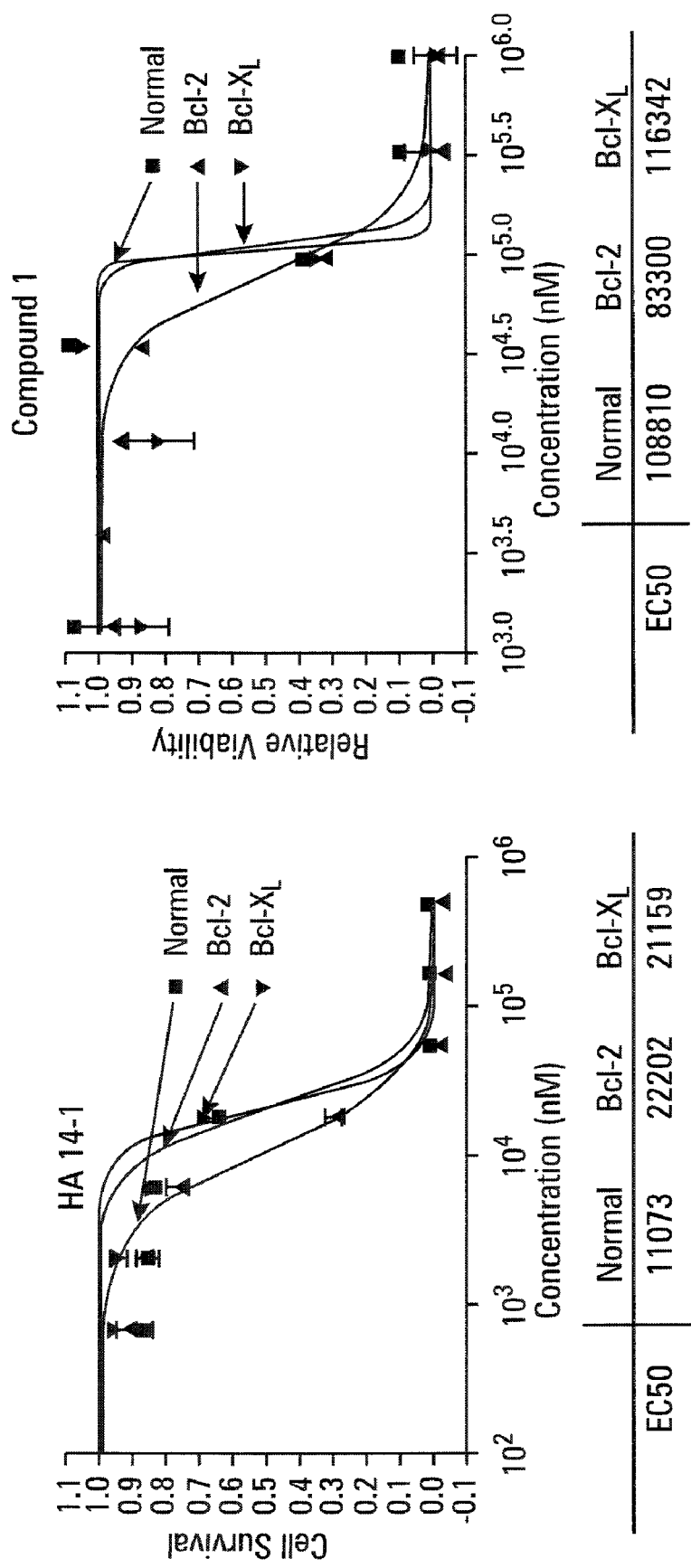
FIG. 3 shows dose-response curves of the growth inhibition induced by HA 14-1 and compound 1 in the three Jurkat cell lines.

Compound 1 was further studied for its capability to overcome drug resistance induced by the over-expression of anti-apoptotic Bcl-2 proteins. Specifically, the in vitro cytotoxicity of compound 1 against three Jurkat cells (normal, over-expressing Bcl-2, or over-expressing Bcl-$X_L$) were evaluated. The two Jurkat cells with the over-expression of Bcl-2 or Bcl-$X_L$ have been established to be resistant to standard chemotherapies and show no resistance to HA 14-1 (see Doshi, J. M.; Tian, D.; Xing, C. J. Med. Chem. 2006, 49, 7731-7739). As shown in FIG. 3, the over-expression of Bcl-2 or Bcl-$X_L$ induced no resistance to compound 1, further indicating that compound 1 may antagonize the anti-apoptotic Bcl-2 proteins as HA 14-1 does.

Figure 4:
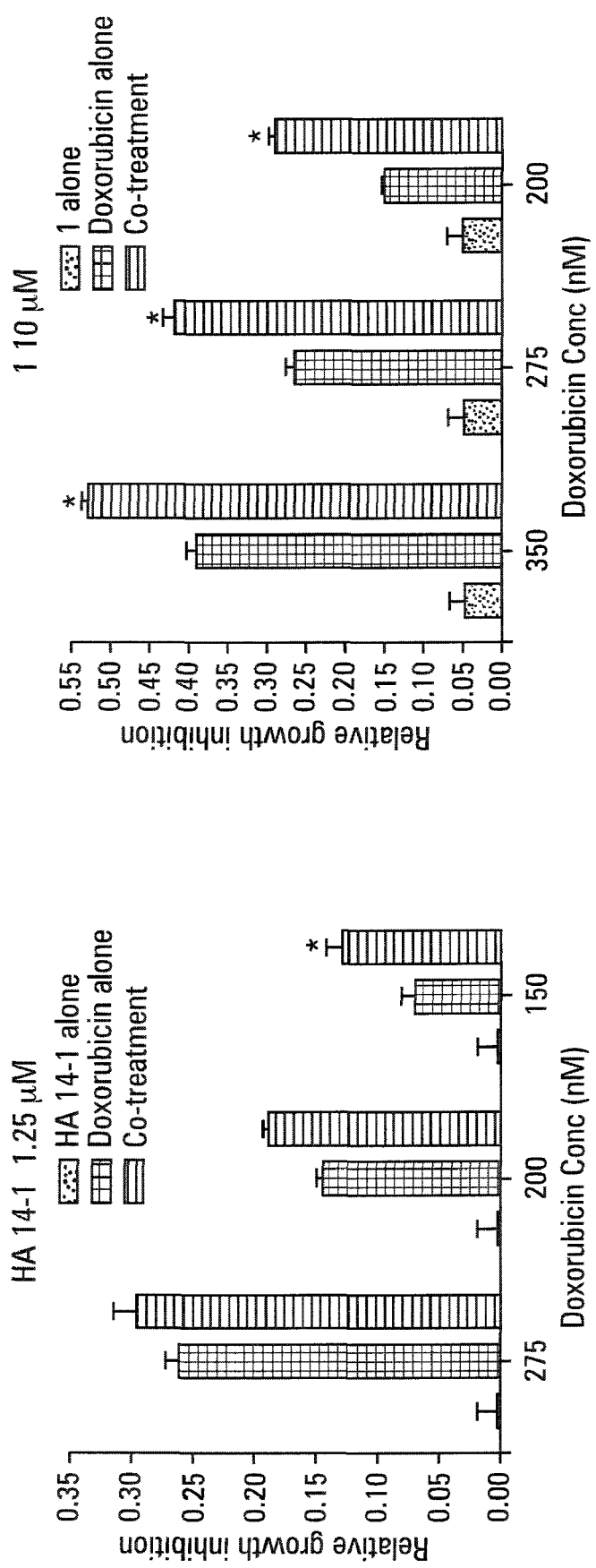
FIG. 4 depicts the inhibition of growth in Jurkat cells induced by HA 14-1 or compound 1 alone, doxorubicin alone, and the combination (* indicates P<0.05).

Finally, compound 1 was analyzed for its capability in sensitizing tumor cells to standard chemotherapies. As HA 14-1 was established to sensitize various tumor cells to doxorubicin, compound 1 was tested in parallel with HA 14-1 for the potential synergism to doxorubicin in Jurkat cells. Briefly, the cytotoxicity of doxorubicin alone, compound 1 alone, or the combination of both to Jurkat cells were evaluated. Both HA 14-1 and compound 1 are able to synergize doxorubicin against Jurkat cells (FIG. 4).

Figure 5:
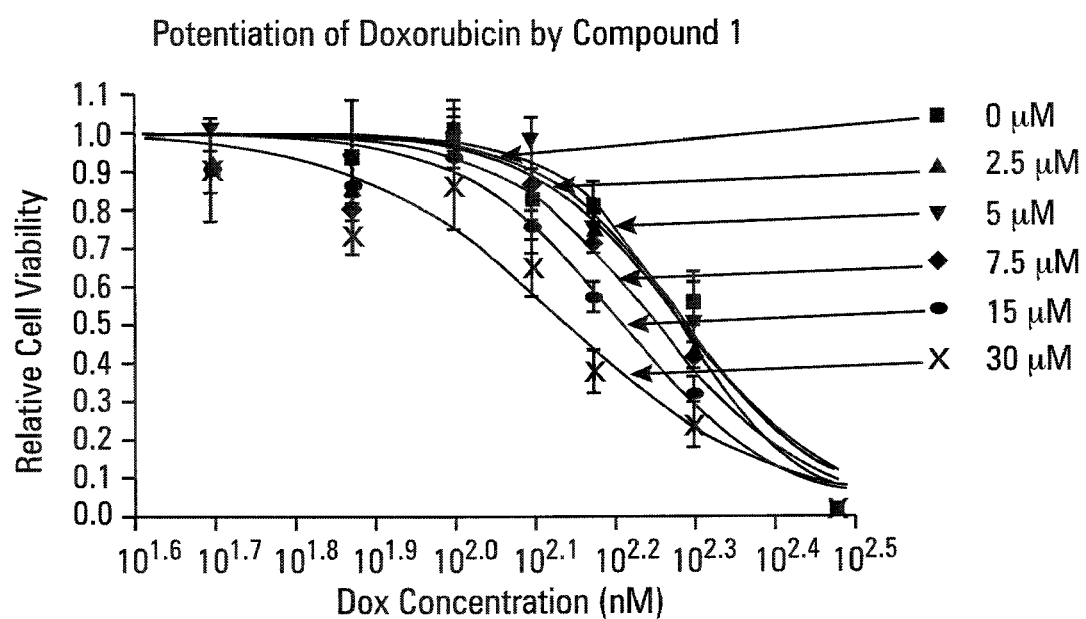
FIG. 5 depicts the potentiation of doxorubicin by compound 1 in Jurkat cells. With 30 µM, compound 1 can potentiate doxorubicin by 1.4 fold.

This study established that compound 1 can function as a chemosensitizer in combination cancer therapy. The synergism of compound 1 was further supported by the dose-response potentiation of doxorubicin (FIG. 5).

Figure 6:
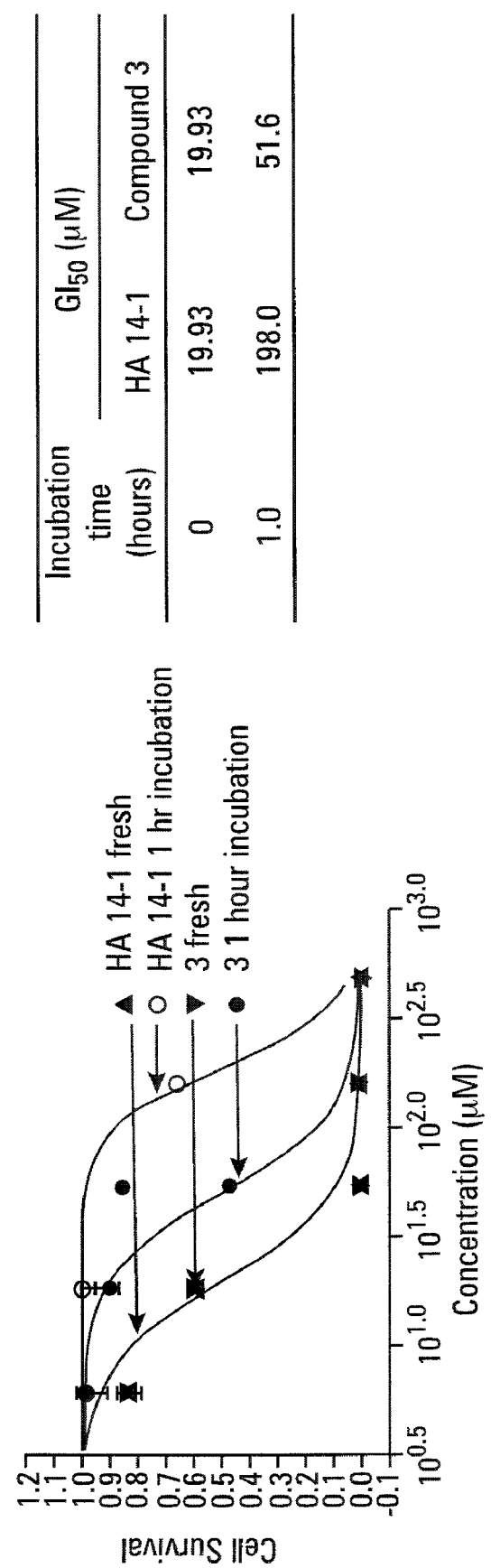
FIG. 6 shows dose-response curves of the growth inhibition by fresh and incubated samples of compound 3.

The stability of compound 3 (Example 1) was evaluated using the in vitro cytotoxicity assay described below. As shown in FIG. 6, compound 3 was more stable than HA 14-1 as one hour incubation only caused 2.5 fold loss of cytotoxicity for compound 3 while HA 14-1 lost 10 folds of its activity.

The improved stability of compound 3 over HA 14-1 was further confirmed by evaluating their half lives (Table 2).

TABLE 2

Half-life of HA 14-1 and compound 3 under varying pH conditions.

| Compound | pH | $t_{1/2}$ (min) |
| --- | --- | --- |
| HA 14-1 | 6.0 | 125.4 |
| HA 14-1 | 7.0 | 111.9 |
| HA 14-1 | 8.0 | 73.12 |
| 3 | 6.0 | 165.2 |

To explore whether compound 3 functioned the same as HA 14-1 in inducing cell death, compound 3 was tested for its binding interactions with recombinant Bcl-2, Bcl-$X_L$, and Bcl-w proteins. This was done by using the FP based competition binding assay (see below). It was found that the binding interactions of compound 3 with the anti-apoptotic Bcl-2 proteins were comparable to those of HA 14-1 (Table 3).

TABLE 3

The binding interactions of HA 14-1 and compound 3 with Bcl-2, Bcl-$X_L$, and Bcl-w proteins.

| | Ki ± SEM (μM)[a] | | |
| --- | --- | --- | --- |
| | Bcl-2 | Bcl-$X_L$ | Bcl-w |
| HA 14-1 | 169 ± 18.9 | 58.9 ± 5.3 | 59.32 ± 5.32 |
| 3 | N/D[b] | 55.43 ± 0.88 | 49.38 ± 1.76 |

Figure 7:
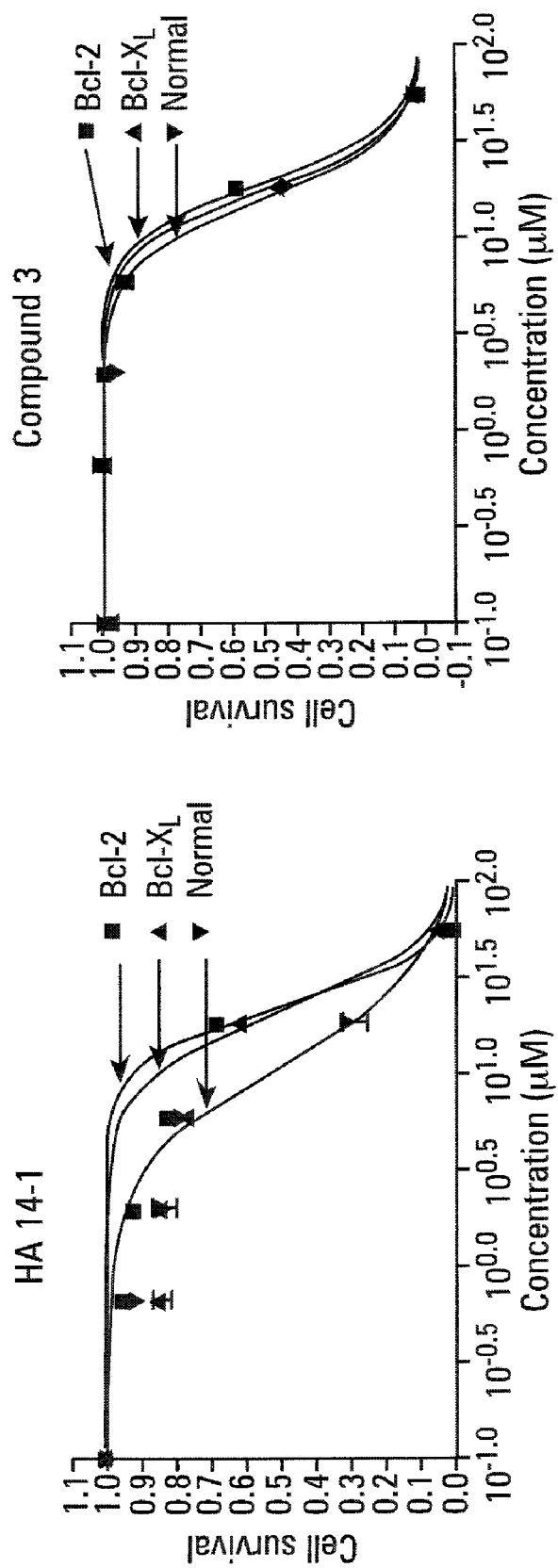
FIG. 7 shows dose-response curves of the growth inhibition induced by HA 14-1 and compound 3 in three Jurkat cell lines.

[a]Results are given as the mean of two independent experiments with triplicate in each experiment
[b]N/D: not determined The ability of compound 3 to overcome the drug resistance induced by the over-expression of anti-apoptotic Bcl-2 proteins by evaluating its cytotoxicity in Bcl-2 or Bcl-$X_L$ over-expressing Jurkat cells was also evaluated. Over-expression of anti-apoptotic Bcl-2 proteins was unable to induce any noticeable resistance to compound 3, further suggesting that compound 3 has a similar mechanism of cytotoxicity as HA 14-1 (FIG. 7).

In Vitro Cytotoxicity Assay

The in vitro cytotoxicity of the test compound was assayed by determining the $GI_{50}$s (the concentration of the compound required to inhibit cell growth by 50%). In brief, Jurkat cells at a density of $10^4$ cells/well were plated in a 96-well plate. A series of 3-fold dilution of the test compound with 1% DMSO in the final cell media was used for the cell treatment (cells treated with media containing 1% DMSO served as a control). An identical set of the test compounds was incubated at 37° C. for the specified time and used along with freshly prepared samples for the cell-viability assay. After 24-hour treatment, the relative cell viability in each well was determined by using CellTiter-Blue Cell Viability Assay kit (a fluorescence assay that measures the reduction of a dye (resazurin) into a fluorescent end product (resorufin) by metabolically active cells—viable cells) (Promega, CA). The $GI_{50}$ of each candidate was determined by fitting the relative viability of the cells to the drug concentration by using a dose-response model in GraphPad software.

Fluorescence Polarization (FP) Assay

The binding interactions of the test compound with Bcl-2, Bcl-$X_L$ and Bcl-w proteins were evaluated using the respective recombinant proteins. The preparation of these recombinant Bcl-2 proteins and fluorescently labeled Bak peptide has been detailed previously (see Doshi, J. M.; Tian, D.; Xing, C. J. Med. Chem. 2006, 49, 7731). The assays were conducted via an optimized protocol established in the laboratory using a GENios Pro plate reader (Tecan US, NC) with all assays performed in triplicate, each assay performed twice (see Doshi, J. M.; Tian, D.; Xing, C. J. Med. Chem. 2006, 49, 7731).

The invention will now be illustrated by the following non-limiting Examples.

General

All commercial reagents and anhydrous solvents were purchased from vendors and were used without further purification or distillation, unless otherwise stated. Analytical thin-layer chromatography (TLC) was performed on EM Science silica gel 60 $F_{254}$ (0.25 mm) Compounds were visualized by UV light and/or stained with either p-anisaldehyde, potassium permanganate, or cerium molybdate solutions followed by heating. Flash column chromatography was performed on Fisher Scientific silica gel (230-400 mesh). IR spectra were recorded on a Nicolet Portege 460 FT-IR instrument. NMR ($^1$H) spectra were recorded on a Varian 300 MHz spectrometer and calibrated using an internal reference. ESI mode mass spectra were recorded on a BrukerBioTOF II mass spectrometer.

Example 1

Synthesis of Ethyl-2-amino-6-bromo-4-(2-cyano-1-ethoxy-1-oxopropan-2-yl)-4H-chromene-3-carboxylate (compound 3)

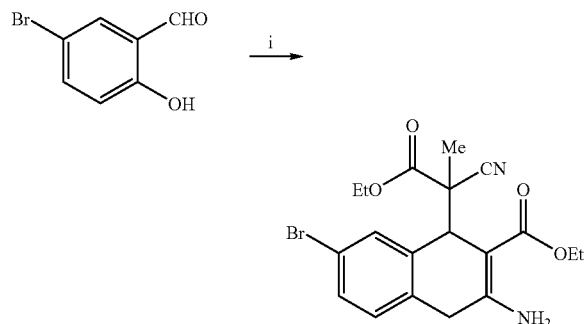

i) α-Methyl ethylcyanoacetate, Ethyl cyanoacetate, EtOH, molecular sieve, 3A, rt In a round-bottom flask equipped with a magnetic stirrer, 5-bromosalicylaldehyde (0.050 g, 0.24 mmol) was dissolved in ethanol (2 ml) and to it molecular sieves 3A (0.1 g) were added. The reaction mixture was stirred followed by the addition of α-methyl ethyl cyanoacetate (0.031 g, 0.24 mmol). The resultant mixture was stirred for another 30 minutes followed by the addition of ethyl cyanoacetate (0.0025 g, 0.024 mmol). After 4 hours, another portion of ethyl cyanoacetate (0.0025 g, 0.024 mmol) was added and the reaction stirred for 12 hours at 25° C. The molecular sieves were then filtered off, and washed with THF (3×5 ml) and methylene chloride (3×5 ml). The combined filtrate was concentrated under vacuum. The crude reaction mixture was washed with hexanes to remove the unreacted 5-bromosalicylaldehyde (0.038 g). Compound 3 was obtained in pure crystalline form by recrystallization using methylene chloride and hexanes. (73% based on consumed 5-bromosalicylaldehyde) TLC (EtOAc:hexane=1:2), $R_f$ 0.33. IR (KBr): 3417, 3300, 2243, 1731, 1676 cm$^{-1}$. $^1$H NMR (CDCl$_3$): δ (ppm): 7.41 (1H, dd, J=2.4, 8.7 Hz, 7-H), 7.33 (1H, d, J=2.4 Hz, 5-H), 6.99 (1H, d, J=8.4 Hz, 8-H), 4.49 (1H, s, 4-H), 4.20 (4H, m, 2×COOCH$_2$CH$_3$), 1.55 (3H, s, CH$_3$), 1.32 (3H, t, J=7.2 Hz, COOCH$_2$CH$_3$), 1.24 (3H, t, J=7.5 Hz, COOCH$_2$CH$_3$). ESI-MS (positive): m/z 444.9, 446.9 (M+Na)$^+$, 317.9, 319.9 (M–CNCHMeCOOEt+Na)$^+$, 295.9, 297.9 (M–CNCHMeCOOEt+H).

Example 2

Synthesis of Ethyl-2-amino-6-bromo-4-(2-ethoxy-2-oxoethyl)-4H-chromene-3-carboxylate (Compound 1)

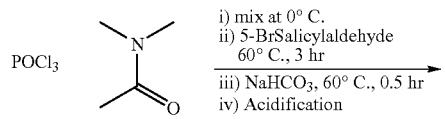

i) mix at 0° C.
ii) 5-BrSalicylaldehyde 60° C., 3 hr
iii) NaHCO$_3$, 60° C., 0.5 hr
iv) Acidification

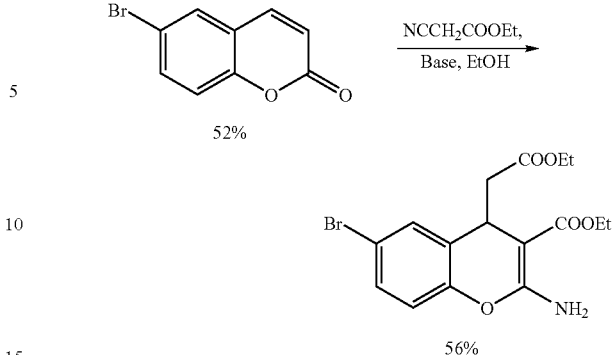

52%

NCCH$_2$COOEt, Base, EtOH

56% a. Synthesis of 6-bromocoumarin: In a round bottom flask equipped with a magnetic stirrer and an ice-water bath, N,N-dimethylacetamide (1.98 mmol, 2 eq) was taken followed by the addition of phosphorus oxychloride (1.98 mmol, 2 eq). The reaction mixture was allowed to stir in the ice bath for 30 minutes followed by addition of 5-bromosalicylaldehyde (0.2 g, 0.99 mmol, 1 eq). The reaction mixture was then heated at 68-70° C. for 3 hours. Following this the reaction mixture was cooled to room temperature and saturated NaHCO$_3$ solution (10 ml) was then added to it. This mixture was subsequently heated at 68-70° C. for another 30 minutes. The crude reaction mixture was cooled and acidified (1 N HCl) to afford an off-white solid which was filtered and washed with water. Yield (56%)

b. Synthesis of Ethyl-2-amino-6-bromo-4-(2-ethoxy-2-oxoethyl)-4H-chromene-3-carboxylate: In a round-bottom flask equipped with a magnetic stirrer freshly cut sodium (0.096 mmol, 1.2 eq) was taken and to it dry ethanol (2 ml) was added followed by the addition of ethyl cyanoacetate (0.192 mmol, 2.4 eq). The reaction mixture was stirred at room temperature under an inert atmosphere for 30 minutes, followed by the addition of a solution of 6-bromocoumarin (0.08 mmol) in ethanol (1 ml). The resulting reaction mixture was stirred at room temperature. The reaction was monitored by TLC and upon consumption of the 6-bromocoumarin, the reaction mixture was concentrated to the half the volume. The reaction mixture was then diluted with water (30 ml) and extracted using methylene chloride (3×20 ml). The organics were combined, dried (MgSO$_4$) and the solvent removed under vacuum, to afford an oil. This crude oil was subjected to column chromatography to afford the pure product as a colorless oil. Yield (52%)

$^1$H NMR Data for compound 1 is included in Example 4.

Example 3

Synthesis of Ethyl-2-amino-6-(3,5-dimethoxyphenyl)-4-(2-ethoxy-2-oxoethyl)-4H-chromene-3-carboxylate

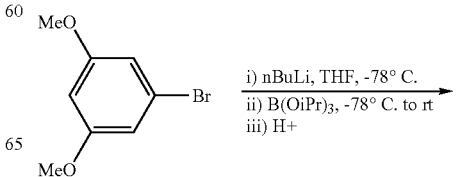

i) nBuLi, THF, -78° C.
ii) B(OiPr)$_3$, -78° C. to rt
iii) H+

-continued

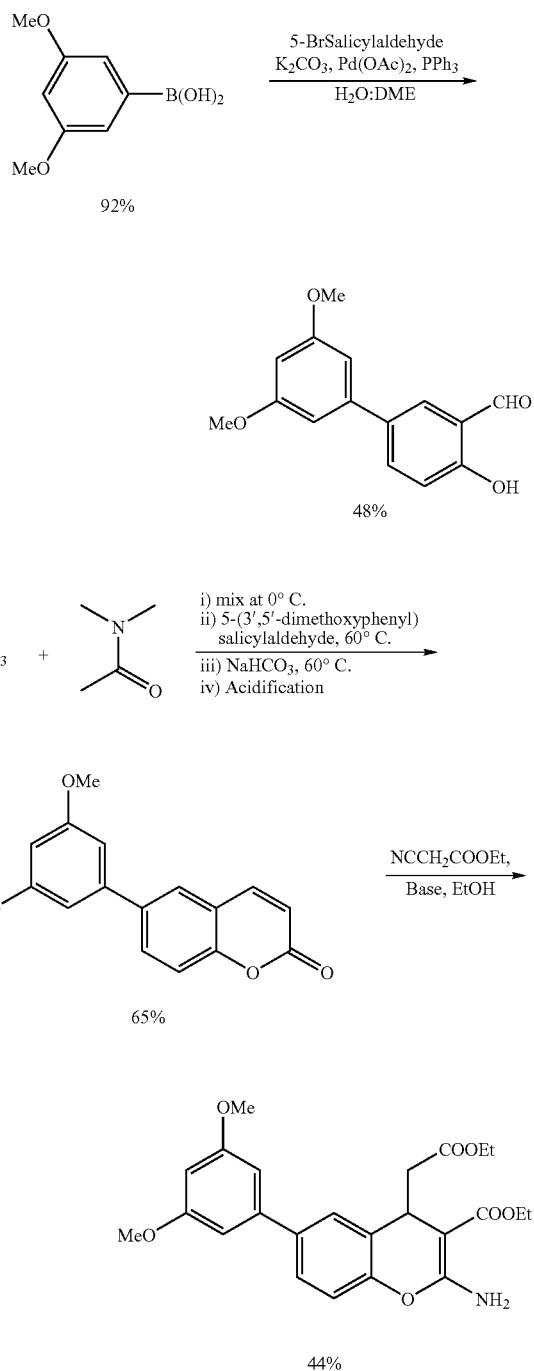

a. Synthesis of 3,5-dimethoxyphenylboronicacid: In a flame dried vessel, cooled under argon 3,5-dimethoxy bromo benzene (3 g, 13.82 mmol) was taken in dry THF (36 ml). The resultant mixture was stirred to obtain a clear solution. This reaction mixture was then cooled to −78° C. and maintained at this temperature for 15 min. This was followed by the addition of n-BuLi (10.92 ml, 2.1M in hexane) following which the reaction was stirred for 30 min. Triisopropyl borate (5.2 g, 27.64 mmol) was then added drop wise and the reaction was stirred at −78° C. for further 2 hr. The reaction was subsequently allowed to warm to room temperature and acidified to pH 2 using sulphuric acid (2M). The resultant mixture was then extracted using ethylacetate. The extracts were combined, dried (MgSO$_4$) and the solvent removed under vacuum. The crude solid was purified using petroleum ether to yield 3,5-dimethoxy phenylboronic acid. Yield (92%).

b. Synthesis of 3,5-dimethoxyphenylsalicylaldehyde: In a round-bottom flask equipped with a magnetic stirrer, 5-bromosalicylaldehyde (1 g, 4.97 mmol), K$_2$CO$_3$ (2.061 g, 14.91 mmol), 3,5-dimethoxyphenylboronic acid (0.9954 g, 5.47 mmol), triphenyl-phosphine (1 mol %) and Pd(OAc)$_2$ (1 mol %) were taken in DME: water (1:1) (12 ml). The mixture was stirred at room temperature under an atmosphere of nitrogen for 24 hours. The reaction mixture was then acidified using HCl (1N) followed by extraction with ethyl acetate. The extracts were combined, dried (MgSO$_4$) and the solvent removed under vacuum. The crude solid was purified by flash chromatography to isolate the desired 3,5-dimethoxyphenyl-salicylaldehyde. Yield (48%).

c. Synthesis of 6-(3,5-dimethoxyphenyl)coumarin: In a vial equipped with a magnetic stirrer and a ice-water bath, N,N-dimethylacetamide (93 μl, 0.99 mmol) was taken followed by the addition of phosphorus oxychloride (0.99 mmol, 1 eq). The reaction mixture was allowed to stir in the ice bath for 30 minutes followed by addition of 3,5-dimethoxyphenylsalicylaldehyde (0.2 g, 1 eq, 0.99 mmol) and subsequent heating of the reaction mixture at 68-70° C. for 3 hours. The reaction mixture was cooled to room temperature followed by the addition of saturated NaHCO$_3$ solution (10 ml) and heating at 68-70° C. for another 30 minutes. The crude reaction mixture was acidified (5.5 N HCl) to afford a yellow solid which was subjected to column chromatography to afford a white solid. Yield (65%)

d. Synthesis of Ethyl-2-amino-6-(3,5-dimethoxyphenyl)-4-(2-ethoxy-2-oxoethyl)-4H-chromene-3-carboxylate: In a round-bottom flask equipped with a magnetic stirrer freshly cut sodium (0.096 mmol, 1.2 eq) was taken and to it dry ethanol (2 ml) was added followed by the addition of ethyl cyanoacetate (0.192 mmol, 2.4 eq). The reaction mixture was stirred at room temperature under an inert atmosphere for 30 minutes, followed by the addition of a solution of 6-(3,5-dimethoxyphenyl)coumarin (0.08 mmol) in ethanol (1 ml). The resulting reaction mixture was stirred at room temperature. The reaction was monitored by TLC and upon consumption of the 6-(3,5-dimethoxyphenyl)coumarin (3 hours), the reaction mixture was concentrated to the half the volume. The reaction mixture was then diluted with water (30 ml) and extracted using methylene chloride (3×20 ml). The organics were combined; dried (MgSO$_4$) and the solvent removed under vacuum, to afford an oil. This crude oil was subjected to column chromatography to afford the pure product as a white solid. Yield (44%)

$^1$H NMR Data for the compound of Example 3 is included in Example 4.

Example 4

The following compounds of Formula (I) wherein R$_4$=R$_5$=H were prepared using procedures similar to those described hereinabove. $^1$H NMR Data for each compound are included following the table.

(I)

| Entry | NR$_c$R$_d$ | R$_2$ | R$_1$ | R$_6$ | R$_3$ | R$_7$ | R$_8$ |
|---|---|---|---|---|---|---|---|
| 1 | NH$_2$ | CO$_2$Et | OEt | H | Br | H | H |
| 2 | NH$_2$ | CO$_2$Et | OEt | H | H | H | H |
| 3 | NH$_2$ | CO$_2$Et | OEt | H | nPr | H | H |
| 4 | NH$_2$ | CO$_2$Et | OEt | H | 4-tBu-C$_6$H$_4$ | H | H |
| 5 | NH$_2$ | CO$_2$Et | OEt | H | Ph | H | H |
| 6 | NH$_2$ | CO$_2$Et | OEt | Ph | H | H | H |
| 7 | NH$_2$ | CO$_2$Et | OEt | H | H | Ph | H |
| 8 | NH$_2$ | CO$_2$Et | OEt | H | H | H | Ph |
| 9 | NHC(O)CH$_3$ | CO$_2$Et | OEt | H | Ph | H | H |
| 10 | N(C(O)CH$_3$)$_2$ | CO$_2$Et | OEt | H | Ph | H | H |
| 11 | NH$_2$ | CO$_2$Et | OEt | H | Ph | H | H |
| 12 | NH$_2$ | CO$_2$iPr | OiPr | H | Ph | H | H |
| 13 | NH$_2$ | CO$_2$Et | -piperidino | H | Ph | H | H |
| 14 | NH$_2$ | CO$_2$Et | -morpholino | H | Ph | H | H |
| 15 | NH$_2$ | CO$_2$Et | -piperazino | H | Ph | H | H |
| 16 | NH$_2$ | CO$_2$Et | —NEt$_2$ | H | Ph | H | H |
| 17 | NH$_2$ | CO$_2$Et | OEt | H | 3,5-(OMe)$_2$-C$_6$H$_3$ | H | H |
| 18 | NH$_2$ | CO$_2$Et | OEt | H | 3-OMe-5-OH-C$_6$H$_3$ | H | H |
| 19 | NH$_2$ | CO$_2$Et | OEt | H | 3,5-(OH)$_2$-C$_6$H$_3$ | H | H |

Entry 1:
$^1$H NMR (CDCl$_3$): δ 7.38 (1H, d, J=2.4 Hz, 5-H), 7.29 (1H, dd, J=2.4, 8.4 Hz, 7-H), 6.84 (1H, d, J=9.0 Hz, 8-H), 6.30 (2H, br. s, NH$_2$), 4.22 (3H, m, 4-H and COOCH$_2$CH$_3$), 4.05 (2H, q, J=7.2 Hz; COOCH$_2$CH$_3$), 2.64 (1H, dd, J=4.8, 15 Hz, HCHCO), 2.57 (1H, dd, J=6.9, 15 Hz, HCHCO) 1.31 (3H, t, J=7.2 Hz, COOCH$_2$CH$_3$), 1.18 (3H, t, J=7.2 Hz, COOCH$_2$CH$_3$).

Entry 2:
$^1$H NMR (CDCl$_3$): δ 7.21 (2H, m, Ar), 7.07 (1H, dt, J=1.5, 7.5, 8.7 Hz), 6.96 (1H, dd, J=1.2, 8.1 Hz) 6.34 (2H, br s, NH$_2$), 4.29 (1H, dd, J=4.8, 7.5 Hz, 4-H), 4.22 (2H, q, J=6.9 Hz, COOCH$_2$CH$_3$), 4.03 (2H, q, J=7.2 Hz, COOCH$_2$CH$_3$), 2.64 (1H, dd, J=4.8, 15.0 Hz, HCHCO), 2.57 (1H, dd, J=7.2, 14.7 Hz, HCHCO), 1.32 (3H, t, J=7.2 Hz, COOCH$_2$CH$_3$), 1.15 (3H, t, J=7.2 Hz, COOCH$_2$CH$_3$).

Entry 3:
$^1$H NMR (CDCl$_3$): δ 7.03 (1H, d, J=1.8 Hz, 5-H), 6.98 (1H, dd, J=2.1 Hz, 8.4 Hz 7-H), 6.86 (1H, d, J=8.4 Hz, 8-H), 6.283 (2H, br, s, NH$_2$), 4.23, (3H, m, 4-H, COOCH$_2$CH$_3$), 4.02 (2H, q, J=6.9 Hz, COOCH$_2$CH$_3$), 2.63 (1H, dd, J=14.7 Hz, 7.5 Hz, CH$_2$), 2.54 (1H, J=14.7 Hz, 7.5 Hz, CH$_2$), 2.51 (2H, t, J=7.5

Hz, CH$_2$CH$_2$CH$_3$), 1.586 (2H, m, CH$_2$CH$_2$CH$_3$), 1.32 (3H, t, J=6.9 Hz, COOCH$_2$CH$_3$), 1.156 (3H, t, J=6.9 Hz, COOCH$_2$CH$_3$), 0.904 (3H, t, J=7.2 Hz CH$_2$CH$_2$CH$_3$).

Entry 4:
$^1$H NMR (CDCl$_3$): δ 7.45 (6H, m, Ar), 7.01 (1H, d, J=8.7 Hz, 8-H), 6.34 (2H, br s, NH$_2$), 4.35 (1H, dd, J=4.5, 6.6 Hz, 4-H), 4.24 (2H, q, J=7.2 Hz, COOCH$_2$CH$_3$), 4.02 (2H, q, J=7.2 Hz, COOCH$_2$CH$_3$), 2.69 (1H, dd, J=5.1, 15.0 Hz, HCHCO), 2.62 (1H, dd, J=6.6, 15.0 Hz, HCHCO), 1.33 (12H, m, C(CH$_3$)$_3$ and COOCH$_2$CH$_3$), 1.13 (3H, t, J=7.2 Hz, COOCH$_2$CH$_3$).

Entry 5:
$^1$H NMR (CDCl$_3$): δ 7.44 (7H, m, Ar), 7.03 (1H, d, J=8.4 Hz, 8-H), 6.32 (2H, br s, NH$_2$), 4.36 (1H, dd, J=4.5, 6.9 Hz, 4-H), 4.24 (2H, q, J=7.2 Hz, COOCH$_2$CH$_3$), 4.02 (2H, q, J=7.2 Hz, COOCH$_2$CH$_3$), 2.70 (1H, dd, J=4.8, 15.0 Hz, HCHCO), 2.62 (1H, dd, J=6.9, 15.0 Hz, HCHCO), 1.34 (3H, t, J=6.9 Hz, COOCH$_2$CH$_3$), 1.12 (3H, t, J=7.2 Hz, COOCH$_2$CH$_3$).

Entry 6:
$^1$H NMR (CDCl$_3$): δ 7.44 (7H, m, Ar), 7.03 (1H, d, J=8.4 Hz, 8-H), 6.32 (2H, br s, NH$_2$), 4.36 (1H, dd, J=4.5, 6.9 Hz, 4-H), 4.23 (2H, q, J=7.2 Hz, COOCH$_2$CH$_3$), 4.02 (2H, q, J=7.2 Hz, COOCH$_2$CH$_3$), 2.69 (1H, dd, J=4.5, 14.7 Hz, HCHCO), 2.62 (1H, dd, J=6.9, 14.7 Hz, HCHCO), 1.33 (3H, t, J=6.9 Hz, COOCH$_2$CH$_3$), 1.12 (3H, t, J=7.2 Hz, COOCH$_2$CH$_3$).

Entry 7:
$^1$H NMR (CDCl$_3$): δ 7.41 (6H, m, Ar), 7.21 (1H, s, Ar), 7.15 (1H, s, Ar), 6.28 (2H, br s, NH$_2$), 4.28 (1H, dd, J=4.5, 7.2 Hz, 4-H), 4.19 (2H, q, J=6.9 Hz, COOCH$_2$CH$_3$), 4.00 (2H, q, J=6.9 Hz, COOCH$_2$CH$_3$), 2.64 (1H, dd, J=4.5, 15 Hz, HCHCO), 2.56 (1H, dd, J=6.9, 15 Hz, HCHCO), 1.28 (3H, t, J=7.2 Hz, COOCH$_2$CH$_3$), 1.12 (3H, t, J=7.2 Hz, COOCH$_2$CH$_3$).

Entry 8:
$^1$H NMR (CDCl$_3$): δ 7.44 (5H, m, Ar), 7.22 (2H, m, Ar), 7.15 (1H, t, J=7.2 Hz, Ar), 6.22 (2H, br s, NH$_2$), 4.36 (1H, dd, J=4.8, 7.5 Hz, 4-H), 4.23 (2H, q, J=7.5 Hz, COOCH$_2$CH$_3$), 4.06 (2H, q, J=7.5 Hz, COOCH$_2$CH$_3$), 2.67 (1H, dd, J=4.2, 14.7 Hz, HCHCO), 2.58 (1H, dd, J=7.5, 14.7 Hz, HCHCO), 1.33 (3H, t, J=7.2 Hz, COOCH$_2$CH$_3$), 1.17 (3H, t, J=7.2 Hz, COOCH$_2$CH$_3$).

Entry 9:
$^1$H NMR (CDCl$_3$): δ 10.980 (1H, s, N—H), 7.45 (7H, m, Ar), 7.20 (1H, d, J=8.1 Hz, 8-H), 4.44 (1H, dd, J=5.1, 7.2 Hz, 4-H), 4.28 (2H, q, J=7.2 Hz, COOCH$_2$CH$_3$), 4.03 (2H, q, J=6.9 Hz, COOCH$_2$CH$_3$), 2.79 (1H, dd, J=5.4, 15.3 Hz, HCHCO), 2.71 (1H, dd, J=7.2, 15.3 Hz, HCHCO), 2.30 (3H, s, NHCOCH$_3$) 1.35 (3H, t, J=7.2 Hz, COOCH$_2$CH$_3$), 1.12 (3H, t, J=7.2 Hz, COOCH$_2$CH$_3$).

Entry 10:
$^1$H NMR (CDCl$_3$): δ 7.45 (7H, m, Ar), 7.10 (1H, d, J=2.7 Hz, 8-H), 4.58 (1H, dd, J=5.4, 6.6 Hz, 4-H), 4.22 (2H, q, J=7.2 Hz, COOCH$_2$CH$_3$), 4.05 (2H, q, J=7.5 Hz, COOCH$_2$CH$_3$), 2.79 (1H, dd, J=5.4, 15.3 Hz, HCHCO), 2.71 (1H, dd, J=6.9, 15.0 Hz, HCHCO), 2.49 (3H, s, N(COCH$_3$), 2.39 (3H, s, N(COCH$_3$), 1.29 (3H, t, J=7.2 Hz, COOCH$_2$CH$_3$), 1.14 (3H, t, J=7.2 Hz, COOCH$_2$CH$_3$).

Entry 11:
$^1$H NMR (CDCl$_3$): δ 7.43 (7H, m, Ar), 7.04 (1H, d, J=8.4 Hz, 8-H), 4.72 (2H, br s, NH$_2$), 4.12 (3H, m, 4-H and COOCH$_2$CH$_3$), 2.78 (1H, dd, J=5.7, 15.3 Hz, HCHCO), 2.71 (1H, dd, J=6, 15.6 Hz, HCHCO), 1.20 (3H, t, J=7.2 Hz, COOCH$_2$CH$_3$).

Entry 12:
$^1$H NMR (CDCl$_3$): δ 7.42 (7H, m, Ar), 7.02 (1H, d, J=8.4 Hz, 8-H), 6.30 (2H, br s, NH$_2$), 5.11 (1H, m, COOCH(CH$_3$)$_2$), 4.92 (1H, m, COOCH(CH$_3$)$_2$), 4.34 (1H, dd, J=4.5, 7.2 Hz, 4-H), 2.67 (1H, dd, J=4.2, 15.0 Hz, HCHCO), 2.61 (1H, dd, J=7.2, 14.7 Hz, HCHCO), 1.33 (3H, d, J=6.6 Hz, COOCH(CH$_3$)$_2$), 1.31 (3H, d, J=6.6 Hz, COOCH(CH$_3$)$_2$), 1.12 (3H, d, J=6.6 Hz, COOCH(CH$_3$)$_2$), 1.04 (3H, d, J=6.6 Hz, COOCH(CH$_3$)$_2$).

Entry 13:
$^1$H NMR (CDCl$_3$): δ 7.51 (3H, m, Ar), 7.38 (4H, m, Ar), 7.03 (1H, d, J=8.4 Hz, 8-H), 6.32 (2H, bs, NH$_2$), 4.40 (1H, dd, J=4.2, 9 Hz, 4-H), 4.24 (2H, q, J=6.9 Hz, COOCH$_2$CH$_3$), 3.59-3.11 (4H, m, N(CH$_2$)$_2$), 2.70 (1H, dd, J=4.5, 13.8 Hz, HCHCO), 2.56 (1H, dd, J=9.3, 13.8 Hz, HCHCO), 1.6-1.3 (6H, m, (CH$_2$)$_3$), 1.34 (3H, t, J=6.9 Hz, COOCH$_2$CH$_3$).

Entry 14:
$^1$H NMR (CDCl$_3$): δ 7.43 (7H, m, Ar), 7.04 (1H, d, J=8.4 Hz, 8-H), 6.34 (2H, br s, NH$_2$), 4.42 (1H, dd, J=5.1, 9.3 Hz, 4-H), 4.24 (2H, q, J=7.2 Hz, COOCH$_2$CH$_3$), 3.49 (4H, m, (OCH$_2$)$_2$), 3.25 (4H, m, (CON(CH$_2$)$_2$), 2.68 (1H, dd, J=4.8, 13.8 Hz, HCHCO), 2.58 (1H, dd, J=9, 13.8 Hz, HCHCO), 1.33 (3H, t, J=6.9 Hz, COOCH$_2$CH$_3$).

Entry 15:
$^1$H NMR (CDCl$_3$): δ 7.43 (7H, m, Ar), 7.04 (1H, d, J=8.1 Hz, 8-H), 6.32 (2H, br s, NH$_2$), 4.41 (1H, dd, J=4.2, 8.7 Hz, 4-H), 4.24 (2H, q, J=6.9 Hz, COOCH$_2$CH$_3$), 3.52-3.18 (2H, m, 2×N(CH$_2$)), 2.69 (6H, m, CH$_2$CO and 2×CH$_2$), 1.33 (3H, t, J=6.9 Hz, COOCH$_2$CH$_3$).

Entry 16:
$^1$H NMR (CDCl$_3$): δ 7.53 (3H, m, Ar), 7.40 (3H, m, Ar), 7.31 (1H, m, Ar), 7.02 (1H, d, J=8.1 Hz, 8-H), 6.31 (2H, br. s, NH$_2$), 4.49 (1H, dd, J=4.2, 9 Hz, 4-H), 4.25 (2H, q, J=6.9 Hz, COOCH$_2$CH$_3$), 3.27 (2H, m, CONCH$_2$CH$_3$), 2.99 (2H, m, CONCH$_2$CH$_3$), 2.61 (1H, dd, J=4.5, 14.1 Hz, HCHCO), 2.53 (1H, dd, J=9, 14.1 Hz, HCHCO) 1.34 (3H, t, J=7.2 Hz, COOCH$_2$CH$_3$), 0.89 (6H, m, 2×CONCH$_2$CH$_3$).

Entry 17:
$^1$H NMR (CDCl$_3$): δ 7.45 (1H, d, J=2.1 Hz, 5-H), 7.39 (1H, dd, J=2.4, 8.4 Hz, 7-H), 7.01 (1H, d, J=8.4 Hz, 8-H), 6.60 (2H, d, J=2.4 Hz, 2',6'-H), 6.45 (1H, t, J=2.1 Hz, 4'-H), 4.35 (1H, dd, J=5.1, 6.9 Hz, 4-H), 4.23 (2H, q, J=6.9 Hz, COOCH$_2$CH$_3$), 4.02 (2H, q, J=6.9 Hz, COOCH$_2$CH$_3$), 3.84 (6H, s, OCH$_3$), 2.69 (1H, dd, J=4.8, 14.7 Hz, HCHCO), 2.62 (1H, dd, J=7.2, 15.0 Hz, HCHCO), 1.33 (3H, t, J=7.2 Hz, COOCH$_2$CH$_3$), 1.13 (3H, t, J=7.2 Hz, COOCH$_2$CH$_3$).

Entry 18:
$^1$H NMR (CDCl$_3$): δ 7.43 (1H, d, J=2.1 Hz, 5-H), 7.37 (1H, dd, J=2.1, 8.4 Hz, 7-H), 6.99 (1H, d, J=8.4 Hz, 8-H), 6.65 (1H, dd, J=1.5, 2.1 Hz, 2'-H), 6.60 (1H, dd, J=1.5, 2.1 Hz, 6'-H), 6.39 (1H, t, J=2.1 Hz, 4'-H), 5.15 (1H, bs, OH), 4.34 (1H, dd, J=4.8, 6.6 Hz, 4-H), 4.23 (2H, q, J=6.9 Hz, COOCH$_2$CH$_3$), 4.02 (2H, q, J=6.9 Hz, COOCH$_2$CH$_3$), 3.83 (3H, s, OCH$_3$), 2.65 (1H, dd, J=4.5, 15 Hz, HCHCO), 2.62 (1H, dd, J=6.9, 14.7 Hz, HCHCO), 1.33 (3H, t, J=6.9 Hz, COOCH$_2$CH$_3$), 1.13 (3H, t, J=6.9 Hz, COOCH$_2$CH$_3$).

Entry 19:
$^1$H NMR (CDCl$_3$): δ 7.36 (1H, d, J=2.1 Hz, 5-H), 7.31 (1H, dd, J=2.1, 8.1 Hz, 7-H), 6.95 (1H, d, J=8.1 Hz, 8-H), 6.58 (2H, d, J=2.1 Hz, 2',6'-H), 6.37 (1H, t, J=2.1 Hz, 4'-H), 5.78 (2H, bs, 2×OH), 4.32 (1H, dd, J=4.8, 6.6 Hz, 4-H), 4.23 (2H, q, J=7.2 Hz, COOCH$_2$CH$_3$), 4.02 (2H, q, J=7.2 Hz, COOCH$_2$CH$_3$), 2.67 (1H, dd, J=4.8, 14.4 Hz, HCHCO), 2.62 (1H, dd, J=6.6, 14.4 Hz, HCHCO), 1.33 (3H, t, J=7.2 Hz, COOCH$_2$CH$_3$), 1.12 (3H, t, J=7.2 Hz, COOCH$_2$CH$_3$).

Example 5

The following compound of Formula (I) was prepared using procedures similar to those described hereinabove.

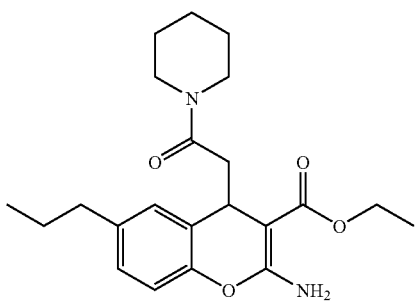

¹H NMR (CDCl₃): δ 7.03 Hz (1H, d, J=2.1 Hz, 5-H), 6.97 (1H, dd, J=2.1, 8.4 Hz, 7-H), 6.86 (1H, d, J=8.1 Hz, 8-H), 6.28 (2H, br, s, NH₂), 4.30 (1H, dd, J=4.2, 9.3 Hz, 4-H), 4.21 (2H, q, J=6.9 Hz, COOCH₂CH₃), 3.51 (2H, m, CH₂N), 3.06-3.33 (2H, m, CH₂N), 2.64 (1H, J=4.5, 13.5 Hz, HCHCO), 2.49 (3H, m, CH₂CH₂CH₃, HCHCO), 1.44-1.65 (8H, m, (CH₂)₃, and CH₂CH₂CH₃), 1.32 (3H, t, J=6.9 Hz, COOCH₂CH₃), 0.91 (3H, t, J=7.2 Hz, CH₂CH₂CH₃).

Example 6

The following compound of Formula (I) was prepared using procedures similar to those described hereinabove.

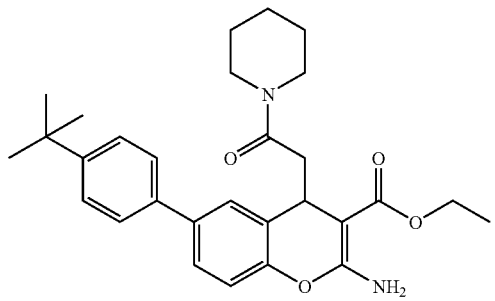

¹H NMR (CDCl₃): δ 7.44 (7H, m, Ar), 7.0, (1H, d, J=8.4 Hz, 8-H), 6.3 (2H, br, s, NH₂), 4.39, (1H, dd, J=4.5, 9.0 Hz, 4-H), 4.23 (2H, q, J=7.2 Hz, COOCH₂CH₃), 3.11-3.34 (2H, m, CH₂N), 3.51 (2H, m, CH₂N), 2.69, (1H, J=4.8, 13.8 Hz, HCHCO), 2.56, (1H, dd, J=9.3, 13.8 Hz, HCHCO), 1.39-1.53 (6H, m, (CH₂)₃), 1.36 (9H, s, (CH₃)₃), 1.34 (3H, t, J=7.2 Hz, COOCH₂CH₃).

Example 7

The following compounds of Formula (I) can be prepared using procedures similar to those described hereinabove.

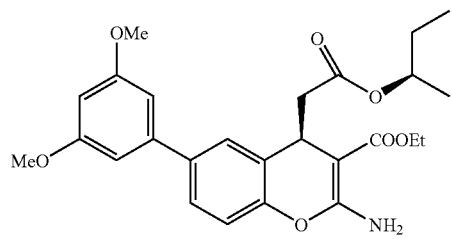

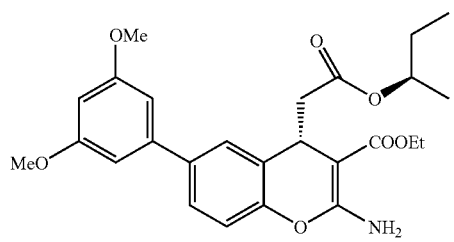

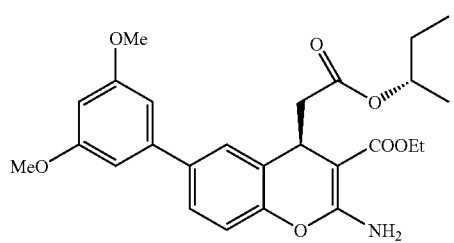

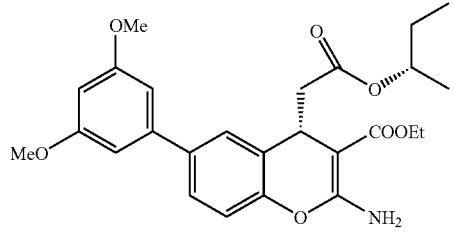

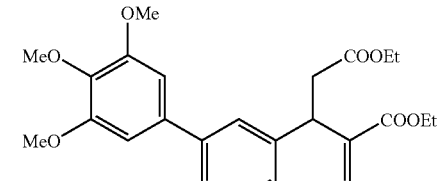

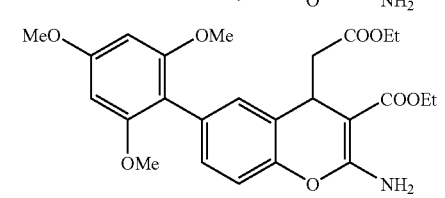

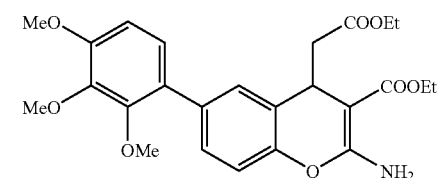

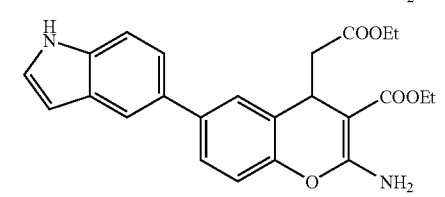

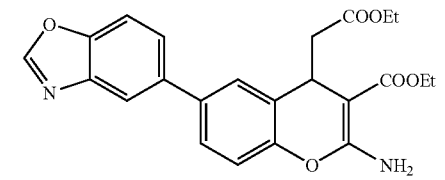

-continued
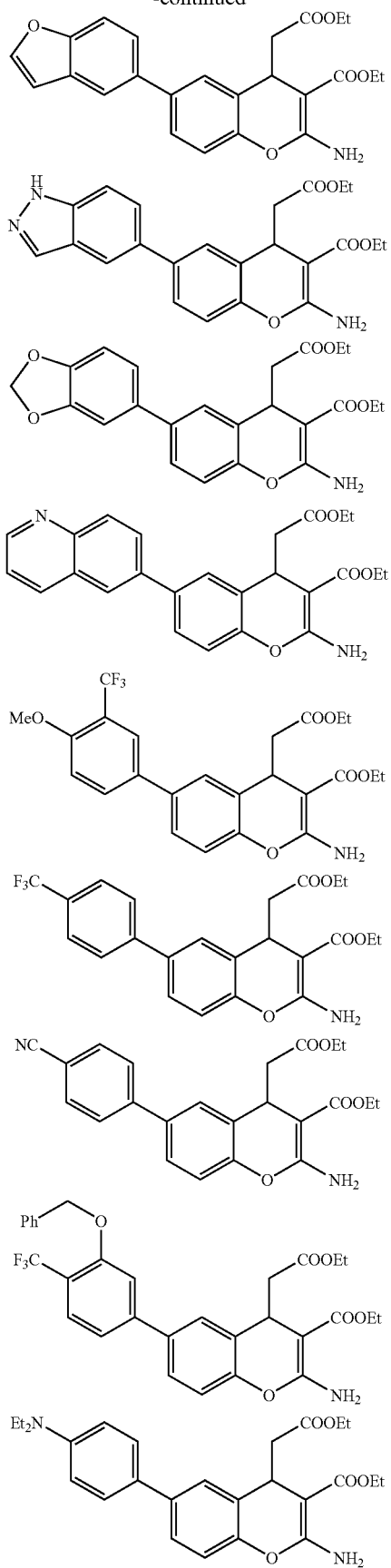
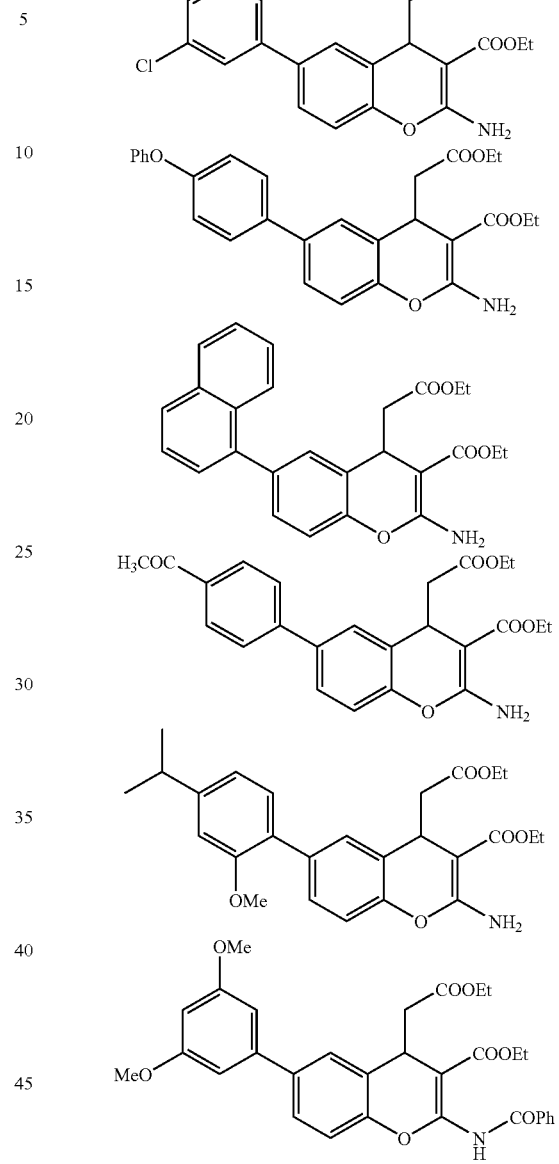
Example 8
The following illustrate representative pharmaceutical dosage forms, containing a compound of formula I ('Compound X'), for therapeutic or prophylactic use in humans.
| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

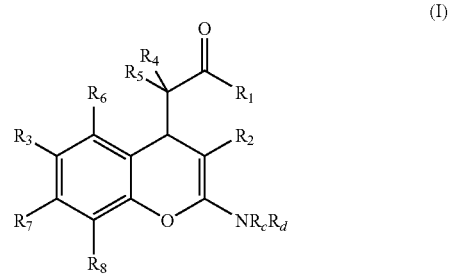

wherein:
$R_1$ is $(C_1-C_6)$alkoxy or $NR_aR_b$;
$R_2$ is cyano, $(C_1-C_6)$alkoxycarbonyl or —C(O)$NR_eR_f$;
$R_3$ is halo, cyano, $(C_1-C_6)$alkyl, cycloalkyl, aryl, heteroaryl, aryl$(C_1-C_6)$alkyl or $(C_1-C_6)$alkoxycarbonyl;
each of $R_6$, $R_7$ and $R_8$ is independently hydrogen, halo, cyano, $(C_1-C_6)$alkyl, cycloalkyl, aryl, heteroaryl, aryl$(C_1-C_6)$alkyl or $(C_1-C_6)$alkoxycarbonyl;
$R_c$ and $R_d$ are independently hydrogen, $(C_1-C_6)$alkyl, $(C_1-C_6)$alkanoyl or arylcarbonyl; or $R_c$ and $R_d$ taken together with the nitrogen to which they are attached form a pyrrolidino, piperidino, piperazino, or morpholino ring;
$R_e$ and $R_f$ are independently hydrogen or $(C_1-C_6)$alkyl; or $R_c$ and $R_d$ taken together with the nitrogen to which they are attached form a pyrrolidino, piperidino, piperazino, or morpholino ring;
$R_4$ and $R_5$ are each hydrogen; or $R_4$ is $(C_1-C_6)$alkyl and $R_5$ is cyano;
$R_a$ and $R_b$ are independently hydrogen or $(C_1-C_6)$alkyl; or $R_a$ and $R_b$ taken together with the nitrogen to which they are attached form a pyrrolidino, piperidino, piperazino, or morpholino ring;
wherein any aryl or heteroaryl of $R_3$, $R_6$, $R_7$ or $R_8$ is optionally substituted with one or more groups independently selected from halo, hydroxy, cyano, $CF_3$, $OCF_3$, $OCHF_2$, $(C_1-C_6)$alkyl, $(C_1-C_6)$alkoxy, $(C_1-C_6)$alkanoyl, aryloxy, $NR_gR_h$, benzyloxy, $(C_1-C_6)$alkoxycarbonyl, and $(C_1-C_6)$alkanoyloxy; and
each $R_g$ and $R_h$ is independently hydrogen or $(C_1-C_6)$alkyl; or $R_g$ and $R_h$ taken together with the nitrogen to which they are attached form a pyrrolidino, piperidino, piperazino, or morpholino ring;
or a salt thereof.

2. A compound of formula (II):

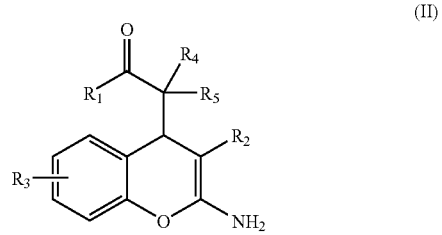

wherein:
$R_1$ is $(C_1-C_6)$alkoxy or $NR_aR_b$;
$R_2$ is cyano, or $(C_1-C_6)$alkoxycarbonyl;
$R_3$ is halo, $(C_1-C_6)$alkyl, aryl, aryl$(C_1-C_6)$alkyl, cyano, or $(C_1-C_6)$alkoxycarbonyl;
$R_4$ and $R_5$ are each hydrogen; or $R_4$ is $(C_1-C_6)$alkyl and $R_5$ is cyano; and each $R_a$ and $R_b$ is independently hydrogen or $(C_1-C_6)$alkyl; or $R_a$ and $R_b$ taken together with the nitrogen to which they are attached form a pyrrolidino, piperidino, piperazino, or morpholino ring;
wherein any aryl of $R_3$ is optionally substituted with one or more groups independently selected from halo, hydroxy, $(C_1-C_6)$alkyl, $(C_1-C_6)$alkoxy, $(C_1-C_6)$alkoxycarbonyl, and $(C_1-C_6)$alkanoyloxy;
or a salt thereof.

3. The compound of claim 1 wherein the compound of formula (I) is a compound of formula (III):

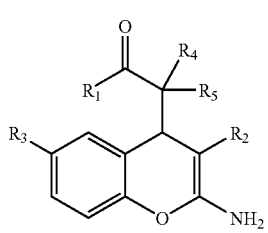

wherein:
$R_1$ is $(C_1-C_6)$alkoxy or $NR_aR_b$;
$R_2$ is cyano, or $(C_1-C_6)$alkoxycarbonyl;
$R_3$ is halo, $(C_1-C_6)$alkyl, aryl, aryl$(C_1-C_6)$alkyl, cyano, or $(C_1-C_6)$alkoxycarbonyl;
$R_4$ and $R_5$ are each hydrogen; or $R_4$ is $(C_1-C_6)$alkyl and $R_5$ is cyano; and
each $R_a$ and $R_b$ is independently hydrogen or $(C_1-C_6)$alkyl; or $R_a$ and $R_b$ taken together with the nitrogen to which they are attached form a pyrrolidino, piperidino, piperazino, or morpholino ring;
wherein any aryl of $R_3$ is optionally substituted with one or more groups independently selected from halo, hydroxy, $(C_1-C_6)$alkyl, $(C_1-C_6)$alkoxy, $(C_1-C_6)$alkoxycarbonyl, and $(C_1-C_6)$alkanoyloxy;
or a salt thereof.

4. The compound of claim 1 wherein $R_1$ is $NR_aR_b$.
5. The compound of claim 1 wherein $R_1$ is ethoxy or isopropoxy.
6. The compound of claim 1 wherein $R_1$ is piperidino.
7. The compound of claim 1 wherein $R_1$ is morpholino, piperazino or diethylamino.
8. The compound of claim 1 wherein $R_2$ is ethoxycarbonyl, isopropoxycarbonyl, or cyano.
9. The compound of claim 1 wherein $R_3$ is aryl, which is optionally substituted with one or more groups independently selected from halo, hydroxy, cyano, $CF_3$, $OCF_3$, $OCHF_2$, $(C_1-C_6)$alkyl, $(C_1-C_6)$alkoxy, $(C_1-C_6)$alkanoyl, aryloxy, $NR_gR_h$, benzyloxy, $(C_1-C_6)$alkoxycarbonyl, and $(C_1-C_6)$alkanoyloxy.
10. The compound of claim 1 wherein $R_3$ is bromo, n-propyl, 4-t-butylphenyl, phenyl, 3,5-dimethoxyphenyl, 3,5-dihydroxyphenyl, 3-hydroxy-5-methoxyphenyl, 3,4,5-trimethoxyphenyl, 2,4,6-trimethoxyphenyl, 1,2,3-trimethoxyphenyl, indol-5-yl, benzoxazol-5-yl, benzofuran-5-yl, indazol-5-yl, 3,4-methylenedioxyphenyl, quinolin-5-yl, 4-methoxy-3-trifluoromethylphenyl, 4-trifluoromethylphenyl, 4-cyanophenyl, 3-benzyloxy-4-trifluoromethylphenyl, 4-(diethylamino)phenyl, 3,5-dichlorophenyl, 4-phenoxyphenyl, naphthyl, 4-acetylphenyl or 4-isopropyl-2-methoxyphenyl.
11. The compound of claim 1 wherein $R_3$ is phenyl, which is optionally substituted with one or more $(C_1-C_6)$alkyl groups.

12. The compound of claim 1 wherein $R_3$ is bromo, propyl, phenyl, 4-tert-butylphenyl, 3-methoxy,5-hydroxyphenyl, 3,5-dihydroxyphenyl, or 3,5-dimethoxyphenyl.
13. The compound of claim 1 wherein $R_4$ and $R_5$ are each hydrogen.
14. The compound of claim 1 wherein $R_4$ is $(C_1-C_6)$alkyl and $R_5$ is cyano.
15. The compound of claim 1 which is

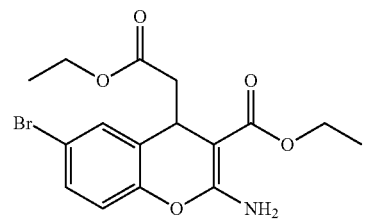

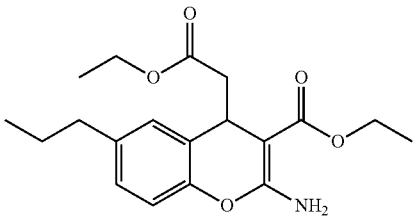

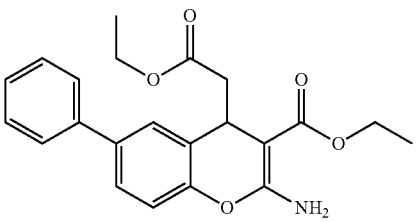

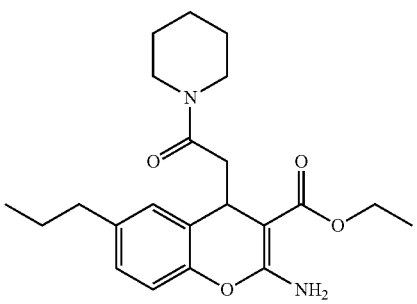

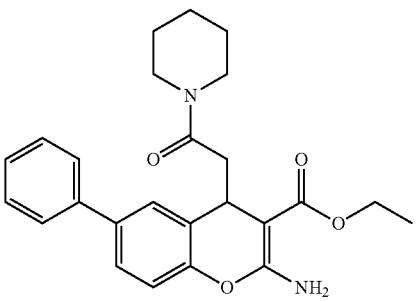

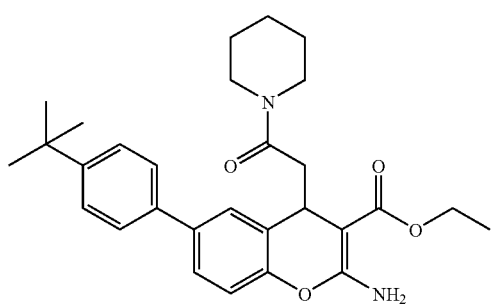
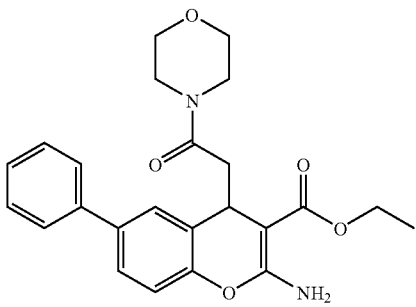
or a salt thereof.
16. The compound of claim 1 which is
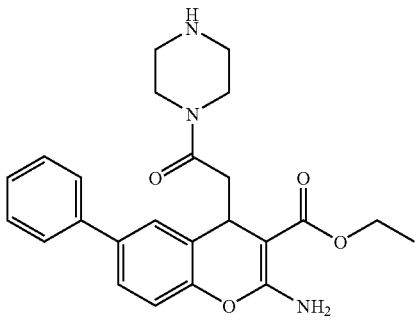
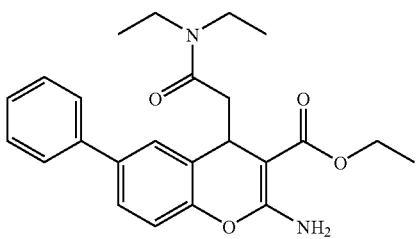
or a salt thereof.

17. The compound of claim 1 which is
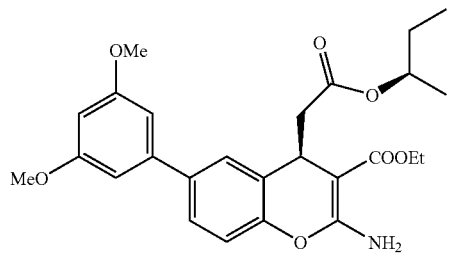
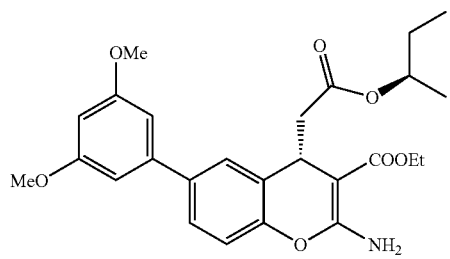
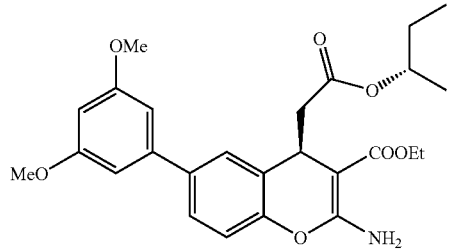
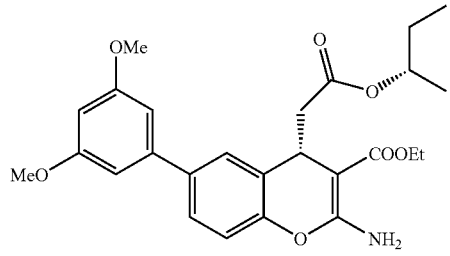
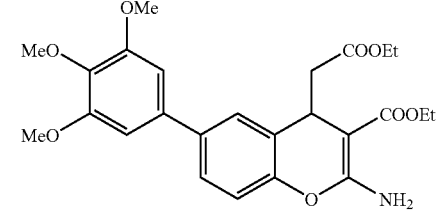
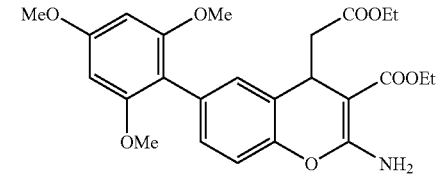
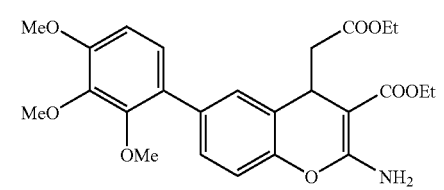
-continued
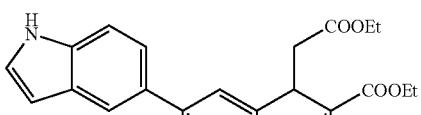
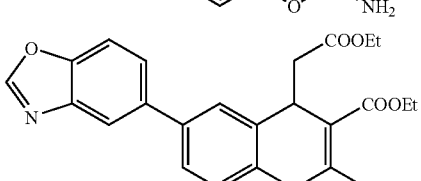
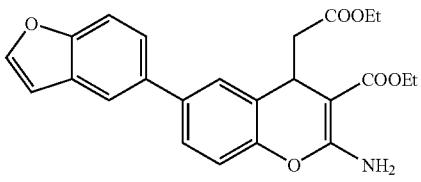
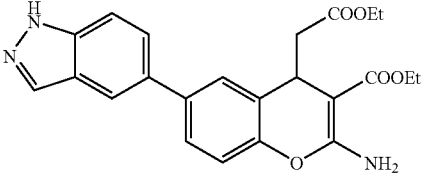
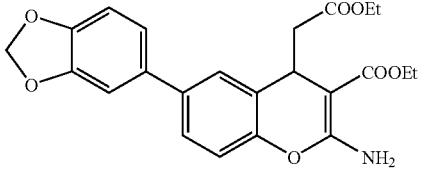
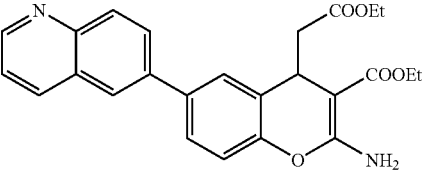
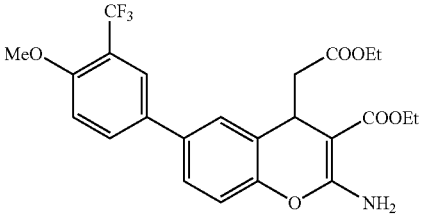
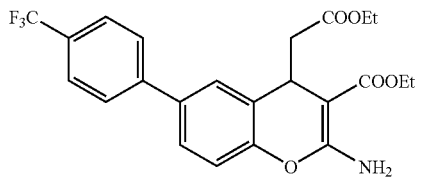
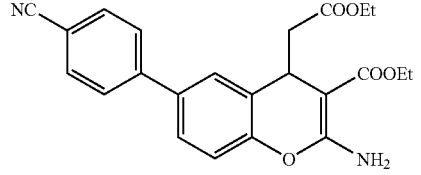

-continued

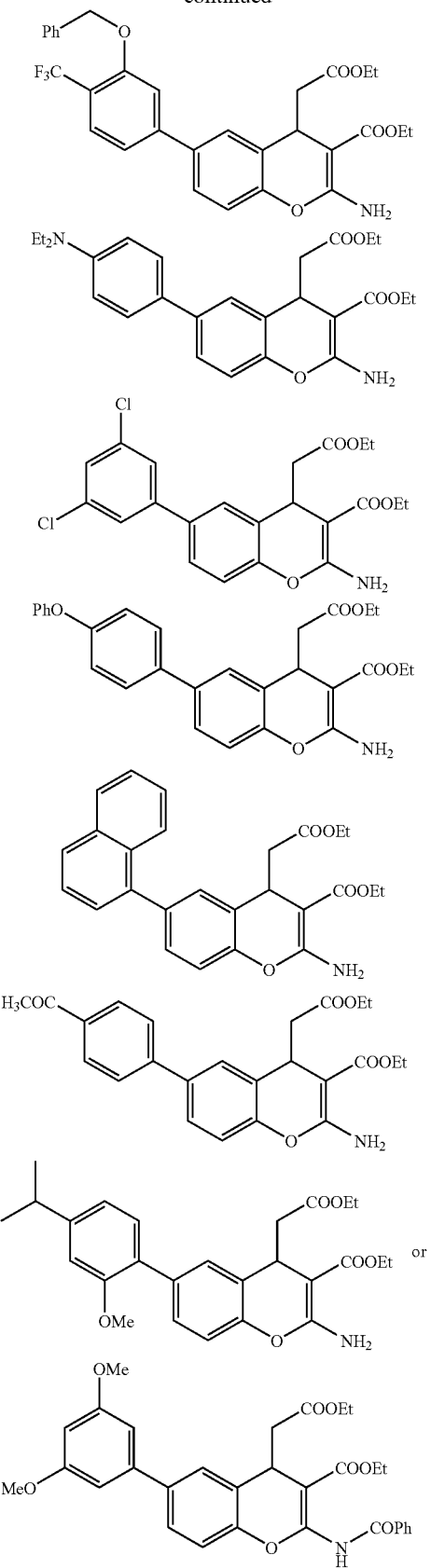

or a salt thereof.

18. A pharmaceutical composition comprising a compound or a pharmaceutically acceptable salt thereof, as described in claim 1, and a pharmaceutically acceptable diluent or carrier.

19. A therapeutic method for treating cancer in a mammal wherein the activity of Bcl-2 protein is implicated and antagonism of its action is desired comprising administering a compound of formula (I):

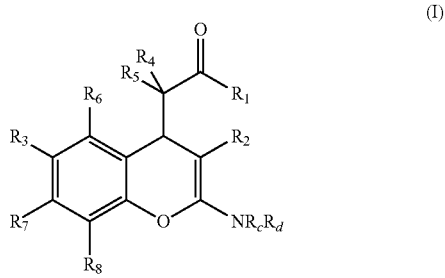

wherein:
$R_1$ is $(C_1-C_6)$alkoxy or $NR_aR_b$;
$R_1$ is cyano, $(C_1-C_6)$alkoxycarbonyl or $—C(O)NR_eR_f$;
each of $R_3$, $R_6$, $R_7$ and $R_8$ is independently hydrogen, halo, cyano, $(C_1-C_6)$alkyl, cycloalkyl, aryl, heteroaryl, aryl $(C_1-C_6)$alkyl or $(C_1-C_6)$alkoxycarbonyl;
$R_c$ and $R_d$ are independently hydrogen, $(C_1-C_6)$alkyl, $(C_1-C_6)$alkanoyl or arylcarbonyl; or
$R_c$ and $R_d$ taken together with the nitrogen to which they are attached form a pyrrolidino, piperidino, piperazino, or morpholino ring;
$R_e$ and $R_f$ are independently hydrogen or $(C_1-C_6)$alkyl; or $R_c$ and $R_d$ taken together with the nitrogen to which they are attached form a pyrrolidino, piperidino, piperazino, or morpholino ring;
$R_4$ and $R_5$ are each hydrogen; or $R_4$ is $(C_1-C_6)$alkyl and $R_5$ is cyano;
$R_a$ and $R_b$, are independently hydrogen or $(C_1-C_6)$alkyl; or $R_a$ and $R_b$ taken together with the nitrogen to which they are attached form a pyrrolidino, piperidino, piperazino, or morpholino ring;
wherein any aryl or heteroaryl of $R_3$, $R_6$, $R_7$ or $R_8$ is optionally substituted with one or more groups independently selected from halo, hydroxy, cyano, $CF_3$, $OCF_3$, $OCHF_2$, $(C_1-C_6)$alkyl, $(C_1-C_6)$alkoxy, $(C_1-C_6)$alkanoyl, aryloxy, $NR_gR_h$, benzyloxy, $(C_1-C_6)$alkoxycarbonyl, and $(C_1-C_6)$alkanoyloxy; and
each $R_g$ and $R_h$ is independently hydrogen or $(C_1-C_6)$alkyl; or $R_g$ and $R_h$ taken together with the nitrogen to which they are attached form a pyrrolidino, piperidino, piperazino, or morpholino ring;
or a pharmaceutically acceptable salt thereof to the mammal.

20. The compound of claim 2 which is
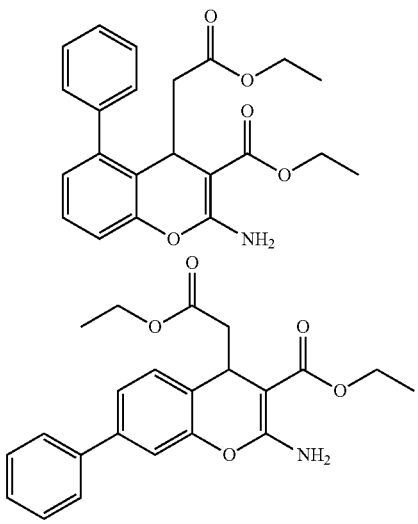
or
or a salt thereof.
21. The method of claim 19 wherein the cancer is acute lymphoblastic leukemia, an acute myelogenous leukemia, a chronic lyphocytic leukemia, breast cancer, colon cancer, liver cancer, lung cancer, pancreatic cancer, or prostate cancer.
* * * * *

UNITED STATES PATENT AND TRADEMARK OFFICE
CERTIFICATE OF CORRECTION

PATENT NO. : 8,394,794 B2
APPLICATION NO. : 12/532804
DATED : March 12, 2013
INVENTOR(S) : Xing et al.

It is certified that error appears in the above-identified patent and that said Letters Patent is hereby corrected as shown below:

In the Claims

In Column 35 Line 55, Claim 10,

Replace:
4-t-butylphenyl

With:
4-*t*-butylphenyl

In Column 36 Line 2, Claim 12,

Replace:
4-tert-butylphenyl

With:
4-*tert*-butylphenyl

In Column 37 Line 37, Claim 16, replace the first figure in the sequence with the following figure:

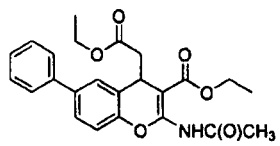

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,394,794 B2  Page 1 of 1
APPLICATION NO. : 12/532804
DATED : March 12, 2013
INVENTOR(S) : Xing et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 684 days.

Signed and Sealed this
First Day of September, 2015

Michelle K. Lee
*Director of the United States Patent and Trademark Office*